United States Patent
Allemann et al.

(10) Patent No.: US 7,455,858 B2
(45) Date of Patent: Nov. 25, 2008

(54) COMPOSITIONS AND METHODS FOR DELIVERY OF PHOTOSENSITIVE DRUGS

(75) Inventors: Eric Allemann, Geneva (CH); Yvette Konan, Geneva (CH); Robert Gurny, Geneva (CH); Ronald E. Boch, Vancouver (CA)

(73) Assignee: QLT Inc., Vancouver (CA)

( * ) Notice: Subject to any disclaimer, the term of this patent is extended or adjusted under 35 U.S.C. 154(b) by 380 days.

(21) Appl. No.: 10/440,505

(22) Filed: May 15, 2003

(65) Prior Publication Data

US 2004/0047913 A1    Mar. 11, 2004

Related U.S. Application Data

(60) Provisional application No. 60/381,474, filed on May 16, 2002.

(51) Int. Cl.
*A61K 9/14* (2006.01)
(52) U.S. Cl. ....................................................... 424/489
(58) Field of Classification Search .................. 424/489
See application file for complete search history.

(56) References Cited

U.S. PATENT DOCUMENTS

| | | | | |
|---|---|---|---|---|
| 4,968,350 A | | 11/1990 | Bindschaedler et al. ..... | 106/170 |
| 5,707,608 A | * | 1/1998 | Liu ........................... | 424/9.61 |
| 5,798,349 A | | 8/1998 | Levy et al. | |
| 2002/0127224 A1 | | 9/2002 | Chen | |

FOREIGN PATENT DOCUMENTS

| | | |
|---|---|---|
| EP | 0 276 121 | 7/1988 |
| WO | WO 97 10811 | 3/1997 |

OTHER PUBLICATIONS

Scoles, P.D. et al., The preparation of sub-200nm poly(lactide-co-clycolide) microspheres for site-specific drug delivery, 1993, J. of Controlled Release, 25, 145-153.*
Allemann et al., Eur. J. Pharm. Biopharm. 39(5):173-191 (1993).
Allemann, E. et al., "In Vitro Extended-Release Properties of Drug Loaded Poly(D,L-Lactic Acid) Nanoparticles Produced by a Salting-out Procedure" Pharm. Res. 10:1732-1737 (1993b).
Allemann, E. et al., "Distribution, Kinetics and Elimination of Radio-activity after Intravenous and Intramuscular Injection of 14C-Savoxepine Loaded Poly(D,L-Lactic Acid) Nanospheres to Rats" J. Controlled Release 29:97-104 (1994).
Allemann, E. et al., "Biodegradable Nanoparticles of Poly(Lactic Acid) and Poly(Lactic-Co-Glycolic Acid) for Parenteral Administration" *In Pharmaceutical Dosage Forms: Disperse Systems* (Lieberman, H. et al., Eds.) Marcel Dekker, Inc. New York 3: 163-193 (1998).

(Continued)

*Primary Examiner*—Konata M. George
(74) *Attorney, Agent, or Firm*—Morrison & Foerster LLP

(57) ABSTRACT

The invention provides nanoparticles containing photosensitizers and their use in the field of photodynamic therapy (PDT). The invention also provides methods for the preparation of such nanoparticles as well as for their sterilization.

19 Claims, 3 Drawing Sheets

OTHER PUBLICATIONS

Athanasiou, K. and Niederauer, G., "Sterilization, Toxicity, Biocompatibility and Clinical Applications of Polylactic Acid/Polyglycolic Acid Copolymers" Biomaterials 17:93-102 (1996).

Beck, L. et al., Obstet. Gynecol. 147:815-821 (1983).

Bindschaedler et la., J. Pharm. Sci. 77(8):696-698 (1998).

De Chasteigner, S. et al., "Gastro-Intestinal Tolerance Study of a Freeze-Dried Oral Dosage Form of Indomethacin-Loaded Nanocapsules" S. T. P. Pharma Sciences 5:242-246 (1995).

De Chasteigner, S. et al., "Freeze-Drying of Itraconazole-Loaded Nanosphere Suspensions: A Feasibility Study" Drug Dev. Res. 116-124 (1996).

DeLuca, P. and Boylan, J., "Formulation of Small Volume Parenterals" In *Pharmaceutical Dosage Forms: Parenteral Medications* Avis, K., et al., (eds.) M. Dekker, Inc. New York 1:139-201 (1984).

Douglas, S. et al., "Nanoparticles in Drug Delivery" CRC Crit. Rev. in Ther. Drug Carrier Syst. 3:233-260 (1987).

El-Samaligy, M. and Rohdewald, P., "Triamcinolone Diacetate Nanoparticles, Sustained Release Drug Delivery System Suitable for Parental Administration" Pharm. Acta. Helv. 57(7):201-4 (1982).

Harmia, T. et al., "Nanoparticles as Drug Carriers in Ophthalmology" Pharm. Acta. Helv. 62:322 (1987).

Hausberger, A. et al., "Gamma Irradiation Effects on Molecular Weight and In Vitro Degradation of Poly(D,L-Lactide-Co-Glycolide) Microspheres" Pharm. Res. 12:851-856 (1995).

Jalil, R., "Biodegradable Poly(Lactic Acid) and Poly(Lactide-Co-Glycolide) Polymers in Sustained Drug Delivery" Drug Dev. Ind. Pharm. 16:2353 (1990).

Kattan, J. et al., "Phase I Clinical Trial and Pharmacokinetic Evaluation of Doxorubicin Carried by Polyisohexylcyanoacrylate Nanoparticles" Invest. New Drugs 10:191-199 (1992).

Kawashima, Y. et al., "Properties of a Peptide Containing DL-Lactide/Glycolide Copolymer Nanospheres Prepared by Novel Emulsion Solvent Diffusion Methods" Eur. J. Pharm. Biopharm. 45:41-48 (1998).

Konan et al., "Preparation and Characterization of Sterile Sub-200 nm Meso-Tetra (4-hydroxylphenyl) Porphyrin-Loaded Nanoparticles for Photodynamic Therapy" Eur. J. Pharma. and Biopharma. 55(1):115-124 (2003).

Konan et al., "Enhanced Photodynamic Activity of Meso-Tetra (4-Hydroxyphenyl) Porphyrin by Incorporation into Sub-200 nm Nanoparticles" Eur. J. Pharma. Sciences: Official J. of Eur. Fed. For Pharma. Sciences 18(3-4):241-249 (2003).

Konan et al., "Encapsulation of p-THPP into Nanoparticles: Cellular Uptake, Subcellular Localization and Effect of Serum on Photodynamic Activity" Photochem. and Photobio. 77(6):638-644 (2003).

Mohr, D. et al., "Gamma Irradiation for Terminal Sterilization of 17-Estradiol Loaded Poly-(D,L-Lactide-Co-Glycolide) Microparticles" J. Control. Rel. 61:203-217 (1999).

Montanari, L. et al., "Gamma Irradiation Effects on Poly(D,L-Lactide-Co-Glycolide) Microspheres" J. Control. Rel. 56:219-229 (1998).

Rodrigues Jr., J. et al., "Primaquine-Loaded Poly(Lactide) Nanoparticles: Physicochemical Study and Acute Tolerance in Mice" Int. J. Pharm. 126:253-260 (1995).

Rolland, "Clinical Pharmacokinetics of Doxorubicin in Hepatoma Patients after a Single Intravenous Injection of Free or Nanoparticles Bound Anthracycline" Int. J. Pharm. 54:113-121 (1989).

Scholes, P. et al., "The Preparation of Sub-200 nm Poly(Lactide-Co-Glycolide) Microspheres for Site-Specific Drug Delivery" J. Control. Rel. 25:145-153 (1993).

Smith, A. and Hunneyball, I. et al., "Evaluation of Poly(Lactic Acid) as a Biodegradable Drug Delivery System for Parenteral Administration" Int. J. Pharm. 30:215-220 (1986).

Tasset, C. et al., "Polyisobutylcyanoacrylate Nanoparticles as Sustained Release System for Calcitonin" J. Control. Rel. 33:23 (1995).

Vert, M., "Structure et Comportement des Polymeres. Exemples des Polymeres Bioresorbables" S.T.P. Pharma 3:216-222 (1987).

Vert, M. et al., "Something New in the Field of PLA/GA Bioresorbable Polymers?" J. Control. Rel. 53:92 (1998).

Volland, C. et al., "The Influence of Terminal Gamma-Sterilization on Captopril Containing Poly(D,L-Lactide-Co-Glycolide) Microspheres" J. Control. Rel. 31:293-305 (1994).

Yoo, H. et al., "Biodegradable Nanoparticles Containing Doxorubicin-PLGA Conjugate for Sustained Release" Pharm. Res. 16:1114 (1999).

Cook et al., Photochemistry and Photobiology (1995) 62(3):542-545.

Saltzman, *Drug Delivery: Engineering Principles for Drug Therapy*, Oxford University Press, 2001, pp. 334-345 (Appendix A).

* cited by examiner

COMPOSITIONS AND METHODS FOR DELIVERY OF PHOTOSENSITIVE DRUGS

RELATED APPLICATIONS

This application claims benefit of priority from U.S. Provisional Patent Application 60/381,474, filed May 16, 2002, which is hereby incorporated by reference as if fully set forth.

TECHNICAL FIELD

The invention relates to the field of photodynamic therapy (PDT), and in particular to compositions and methods for the parenteral or local delivery of therapeutic photosensitive compounds. Biodegradable nanoparticles compositions containing polyester polymers are provided to deliver photosensitizers as the activatable agent in PDT. Also provided are methods for the preparation and use of such nanoparticle compositions.

BACKGROUND ART

Photodynamic therapy (PDT) is a two step process. First, a photoactivatable drug or agent (interchangeably referred to herein as a "photosensitizer" or "PS") is administered either systemically or locally. Then after an appropriate interval, during which time the photoactivatable drug accumulates in target tissue more than in non-target tissue, irradiation with electromagnetic irradiation, such as visible (non thermal) light, is applied to a treatment area for a short period of time. During the time of irradiation the drug acts as a catalytic photosensitizer, absorbing a photon and transferring this energy to oxygen. This process converts the available stable, benign molecular oxygen into cytotoxic singlet oxygen or other toxic oxygen species, which kills targeted cells or otherwise alters or modulates cellular activity in them. PDT is widely used in the treatment of cancer, and in certain ophthalmic conditions characterized by neovascularization in the eye, for example, in age related macular degeneration (AMD). Visudyne® (Novartis Ophthalmics, Inc.), containing a green porphyrin photosensitizer, verteporfin, is approved in many countries for the treatment of choroidal neovascularization and AMD.

While many photosensitizers are hydrophobic or otherwise water insoluble, they are often needed in water based or otherwise aqueous environments in which target cells are found. As such, multiple systems have been developed as delivery vehicles for such agents. Preferably, pharmaceutically acceptable delivery vehicles for photosensitizers are manufactured simply and cost effectively, while maintaining the properties of efficient drug delivery.

Nanoparticles are solid colloidal particles formed by the association of suitable polymers. Nanoparticles are produced by mechanical or chemical means and can be formulated to contain an active substance such as a hydrophobic drug in association with the polymers. Nanoparticles thus provide an alternative to other colloidal carriers such as liposomes, micelles, niosomes (non-ionic surfactant vesicles), and microemulsions.

Synthetic polymers used in the preparation of nanoparticles include polyesters such as poly (lactic acid), poly (lactide-co-glycolide) and poly (ε-caprolactone) (U.S. Pat. No. 4,968,350). Nanoparticles are usually prepared using one of the following methods: emulsion evaporation, solvent displacement, emulsification-diffusion and the salting-out technique. These techniques are similar in that they involve an organic solution containing the nanoparticle components and an aqueous component containing stabilizers that act as the dispersion medium for the nanoparticles.

Biodegradable nanoparticles based on polyester polymers such as poly(D,L-lactide-co-glycolide) (PLGA) and poly(D,L-lactide) (PLA) have been widely investigated as parenteral delivery systems (Allémann et al., 1998; Kawashima et al., 1998; Rodrigues Jr et al., 1995; Scholes et al., 1993; Smith et al., 1986). Polyester polymers, approved by the Food and Drug Administration, are of interest due to their physico-chemical and biological properties (Vert 1987; Vert et al., 1998). Nanoparticles have been used to modify the pharmacokinetics of drugs, as detailed in the following: Roland, Clinical pharmacokinetics of doxorubicin in hepatoma patients after a single intravenous injection of free or nanoparticles bound anthracycline, *Int.J.Pharm.*, 54:113(1989); J. Kattan, J. P. Droz, P. Couvreur, J. P. Marino, A. B. Laroze, P. Rougier, P. Brault, H. Vranckx, J. M. Grognet, X. Morge and H. Sancho-Carnier, Phase I clinical trial and pharmacokinetic evaluation of doxorubicin carried by polyisohexylcyanoacrylate nanoparticles, *Invest. New Drugs*, 10:191 (1992); H. S. Yoo, J. E. Oh, T. G. Park, Biodegradable nanoparticles containing doxorubicin-PLGA conjugate for sustained release, *Pharm. Res.*, 16:1 114 (1999); E. Allémann, R. Gurny, E. Doelker, F. S. Skinner, H. Schutz, Distrubution, kinetics and elimination of radioactivity after intravenous and intramuscular injection of 14C-savoxepine loaded poly(D,L-lactic acid) nanospheres to rats, *J. Controlled Release* 29: 97-104 (1994); R. Jalil, Biodegradable poly(lactic acid) and poly (lactide-co-glycolide) polymers in sustained drug delivery, *Drug Dev. Ind. Pharm.*, 16:2353 (1990), C. Tasset; N. Barette; S. Thysman; J. M. Ketelslegers; V. Preat et al , Polyisobutylcyanoacrylate nanoparticles as sustained release system for calcitonin, *J. Control. Rel.*, 33: 23 (1995); T. Harmia; P. Speiser, J. Kreuter, Nanoparticles as drug carriers in ophthalmology, *Pharm. Acta. Helv.*, 62: 322(1987); and M. El-Samaligy; P. Rohdewald, Triamcinolone diacetate nanoparticles, sustained release drug delivery system suitable for parenteral administration *Pharm. Acta. Helv.*, 57(7): 201-4 (1982).

Traditionally, biodegradable nanoparticles have served as depots of entrapped drug which are slowly released from the polymer matrix. This has been thought to be an effect of a slow polymer degradation to result in a slow release of the drug over time. For example, intramuscular injections of long-acting injectable microcapsules composed of poly(DL-lactide)-co-glycolide containing contraceptives into women provided controlled release (Beck LR et al. A. J. *Obstet. Gynecol.* 147, 815-821, 1983). Also, doxorubicin nanoparticles were thought to deposit in an intrahepatic reservoir and slowly release when administered in polyisohexylcyanoacrylate and polymethacrylate nanoparticles (Kattan J. et al. *Investigational New Drugs*, 10, 191-199, 1992, Rolland A *International Journal of Pharmaceutics*, 54, 113-121, 1989).

For parenteral administration, nanoparticulate formulations must meet the pharmacopoeial requirements of sterility. However, sterilization of such polymeric devices by a satisfactory technique remains a challenge. The chemical or physical lability of the polymer matrix usually limits most conventional methods for obtaining acceptable sterile products. For example, sterilization by autoclaving can induce degradation of polyesters and drug by hydrolysis. These polymers are also heat sensitive due to their thermoplastic nature (Athanasiou et al., 1996). Chemical sterilization by gases such as ethylene oxide may result in toxicity problems to toxic residues. Numerous studies have shown the effects of γ-irradiation on the stability and the safety of colloidal carriers based on polyesters, principally microparticles (Hausberger et al., 1995; Mohr et al., 1999; Montanari et al., 1998; Volland et al., 1994). Gamma-irradiation was shown to affect drug loaded polyester microparticle properties in several ways such as radiolytic reactions, chain scission and cross-linking (Volland et al., 1994). These reactions may have consequences on the nominal drug content, the drug release pattern and the bioresorption of the system. Moreover, the encapsulated drug may degrade upon exposure to gamma irradiation. Therefore, the selection of a suitable sterilization method for such type of formulations is crucial to ensure their physical and chemical integrity, their performance and safety in vivo.

As an alternative technique, sterile filtration through 0.22 μm membrane filters has been used for chemically or thermally sensitive materials since it has no adverse effect on the polymer and the drug. The presence of particles with sizes above the sterilization membrane cutoff, however, tends to result in membrane clogging and decreased efficiency of filtration. It would be advantageous to have methods for the preparation of nanoparticles with a mean size significantly below the sterilization membrane cut-off and with a narrow size distribution to avoid membrane clogging. The ability to produce nanoparticles in the size range of 100-150 nm would be attractive for targeting sites located outside the vascular system. Some tumours, which possess a defective microvasculature, exhibit an increased vascular permeability favouring the accessibility of colloidal carriers to extravascular tumoral cells (Douglas et al., 1987).

Citation of documents herein is not intended as an admission that any is pertinent prior art. All statements as to the date or representation as to the contents of these documents is based on the information available to the applicant and does not constitute any admission as to the correctness of the dates or contents of these documents.

DISCLOSURE OF THE INVENTION

The present invention provides photosensitizer-loaded nanoparticles that unexpectedly release the photosensitizer rapidly once the nanoparticles are introduced into an environment containing serum proteins, for example, the bloodstream of a human subject undergoing photodynamic therapy (PDT) treatment. This observation is in contrast to previous uses of nanoparticles for controlled, or time delayed, release of active ingredients from nanoparticles. The nanoparticles of the invention are also small enough to permit efficient sterilization by a filtration process.

The present invention thus also provides methods for the production of photosensitizer-loaded nanoparticles of a mean particle size less than about 220 nm, optionally less than 200 nm, in diameter to enable sterilization by a filtration process. The nanoparticles of the present invention are also sufficiently stable to withstand freeze drying and reconstituting in an aqueous medium for administration.

In one set of embodiments, the invention provides a composition comprising photosensitizer-loaded nanoparticles, wherein the nanoparticles release at least about 50% of the photosensitizer rapidly, preferably within about 60 seconds, after the nanoparticles are introduced into an environment containing serum proteins. In preferred embodiments, the photosensitizer is a green porphyrin.

In another aspect, the invention provides a pharmaceutical composition comprising one or more photosensitizer and one or more polymer that is suitable for the formation of nanoparticles, wherein the nanoparticles have a mean diameter of less than 200 nm. In preferred embodiments, the polymers are poly(D,L-lactide-co-glycolide), also referred to as PLGA, and/or poly(D,L-lactide), also referred to as PLA. In another embodiment, the photosensitizer-loaded nanoparticles are in freeze-dried form. In a preferred embodiment, the nanoparticles are stable after freeze drying and after reconstitution in an aqueous medium.

In yet another aspect, the invention provides a composition comprising green porphyrins and one or more polyester polymer. In preferred embodiments, the green porphyrins are verteporfin, QLT 0069 or QLT 0074. Green porphyrins are, of course, preferably used in combination with PLGA and/or PLA in the practice of the invention.

The surprising discovery that photosensitizer-containing nanoparticles release photosensitizer rapidly (within a few seconds) after being exposed to a serum-containing medium provides a rationale for the use of nanoparticles as a delivery vehicle for photosensitizers. As appreciated by the skilled person, sustained release of photosensitizer is not desirable in a clinical or other therapeutic setting, where a continued state of photosensitization, brought on by slow release of a photosensitizer, is to be avoided to prevent undesirable side effects. Nanoparticles containing therapeutic compounds have previously been utilized for sustained delivery of therapeutic compounds as opposed to rapid release.

The invention thus also provides methods for the use of photosensitizer containing nanoparticles in PDT. The methods comprise administration of the nanoparticles followed by activation of the photosensitizer after its rapid delivery to targeted cells or tissues. Administration is preferably by parenteral means such as, but not limited to, intravenous injection.

MODES OF CARRYING OUT THE INVENTION

Figure 1:
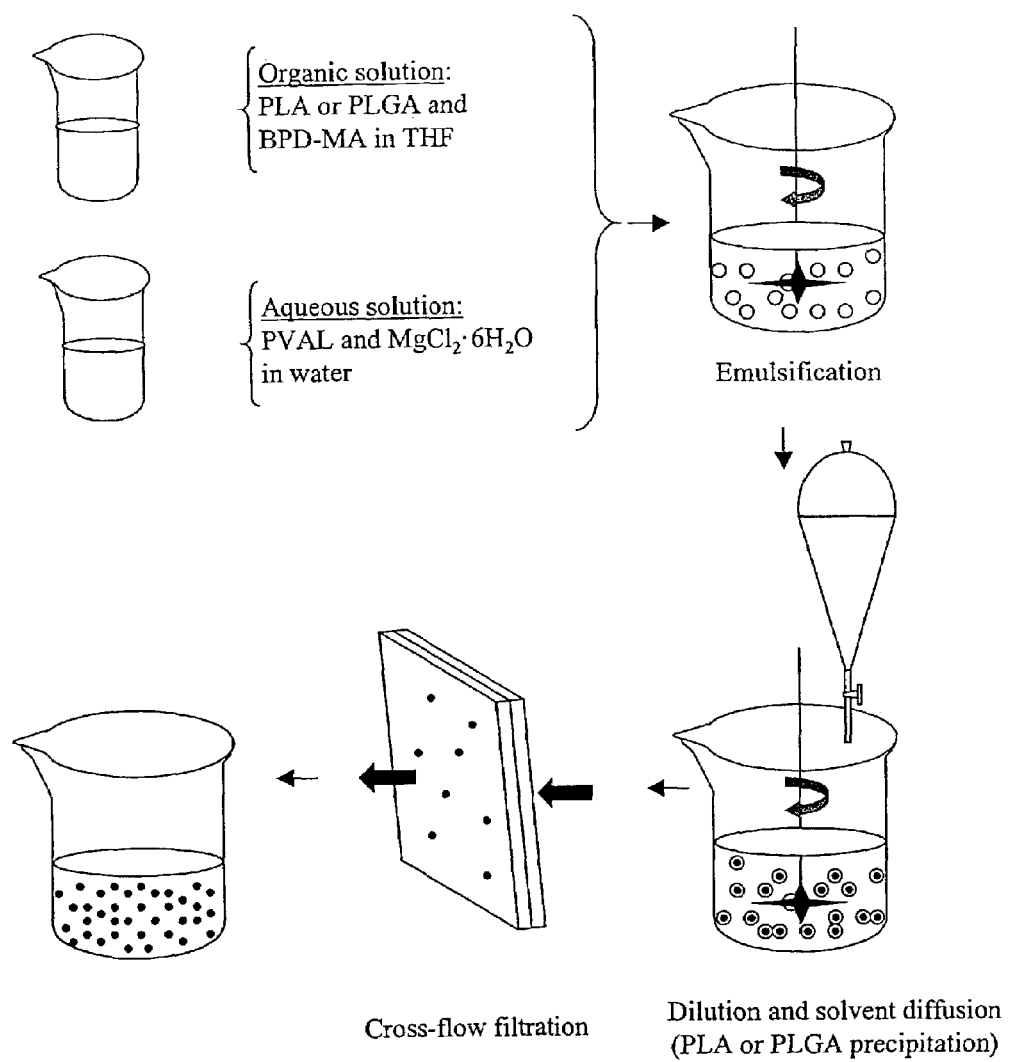
FIG. 1 shows a schematic representation of the process for preparation of nanoparticles.

The present invention is based in part upon the surprising discovery that photosensitizer-containing nanoparticles release photosensitizer rapidly (within a few seconds to a few minutes) after being exposed to a serum-containing medium. It is believed that this is the first instance of a nanoparticle composition having been shown to release a therapeutic compound within a few seconds of exposure to serum. The fact that such nanoparticles release photosensitizer rapidly makes it practical to use photosensitizer-loaded nanoparticles to deliver photosensitizer to a subject being undergoing PDT. In PDT, it is highly desirable to utilize a formulation that releases the photosensitizer rapidly so that it can have maximum activation, can accumulate in target tissue within a few minutes of administration, and then be rapidly cleared from the subject after activation of the photosensitizer by light administration. This avoids the complications of prolonged skin photosensitivity seen in situations where photosensitizer concentrations remain over an extended period. Without being bound by theory, and offered for the benefit of improving the understanding of the invention, the combination of a photosensitizer such as a green porphyrin and a polyester polymer in a nanoparticle may destabilize the nanoparticle such that it readily releases the green porphyrin upon contact with serum. This release may be in the form of a delivery of the photosensitizer from the nanoparticle to lipoproteins within the serum.

Alternatively, and again without being bound by theory, the rapid release of green porphyrin may be due to the sub 220 nm size of the nanoparticles of the invention, which may facilitate the dispersal of photosensitizer. This may suggest that the rapid release phenomenon would be generally applicable to active ingredients or pharmaceutical agents beyond photosensitizers.

As used herein, the term nanoparticles include nanospheres, composed of a polymeric matrix type structure, and nanocapsules, composed of a polymer shell surrounding a liquid core. The "rapid release" of photosensitizer (PS) from a nanoparticle preparation containing them refers to the ability of a PS containing nanoparticle to release or deliver the PS within about 5 minutes after contact with a serum containing medium. Preferably, release of more than 50% of the PS occurs in less than 5 minutes after contact, more preferably in less than about 4 minutes, less than about 3 minutes, less than about 2 minutes, less than about 60 seconds, or less than about 30 seconds. In other embodiments of the invention, the amount of PS released may be more than 60% or more than 70% of the PS present in the nanoparticle. Preferred photosensitizers and nanoparticle forming polymers for the practice of the invention are provided below. "Green porphyrins" refer to porphyrin derivatives obtained by reacting a porphyrin nucleus with an alkyne in a Diels-Alder type reaction to obtain a mono-hydrobenzoporphyrin.

The invention also provides methods for the formulation of PS containing nanoparticles as described below. The disclosed methods include the discovery of means to prepare nanoparticles of a predictably small size and relative uniformity (in size distribution) such that the nanoparticles may be readily sterilized by filtration, such as through a 0.22 micron filter. Preferred nanoparticles of the invention have a mean particle size of less than about 200 nm, more preferably of less than or about 190 nm, less than or about 180 nm, less than or about 170 nm, less than or about 160 nm, less than or about 150, less than or about 140, or less than or about 130 nm in diameter. The use of "diameter" does not indicate that the nanoparticles of the invention are necessarily spherical in shape. Instead the term refers to the approximate average width of nanoparticles as disclosed herein.

The nanoparticles of the invention may also be dehydrated for improved stability and storage. Preferred means of dehydration include freeze drying or lyophilization, although other methods may be used. Optionally, a lyoprotectant is included as an additive in the nanoparticles of the invention to improve stability during a lyophilization process. Such additives may further serve to improve rehydration (or redispersion) of lyophilized nanoparticles prior to use.

The invention further provides for the use of photosensitizer containing nanoparticles as a vehicle to deliver photosensitizers in applications known in the art. Preferred applications of the invention include therapeutic uses, such as photodynamic therapy (PDT) as known in the art, where photosensitizer selection and activation are conducted by the skilled person in combination with the use of nanoparticles to deliver the photosensitizer. Preferably, the nanoparticles are used to deliver the photosensitizer to a serum containing fluid or tissue of a subject undergoing PDT.

Polymers for Making Nanoparticles

Non-limiting examples of suitable polymers for the formation of nanoparticles of the invention include a pharmaceutically acceptable homopolymer or copolymer from monomers selected from the group consisting of L-lactide N or S; D-lactide S; D,L-lactide S; glycolide S; or trimethylene carbonate. Such polymers are marketed under MEDISORB (Registered Trademark of Medisorb Technologies Inc.) PURASORB (Registered Trademark of PURAC Biochem) or RESOMER (Registered Trademark of Boehringer Ingelheim, Germany). Suitable MEDISORB polymers are those of the L or DL series, such as 100 L or DL, or 8515, 7525, 6535 or 5050 DL; RESOMER homopolymers for use in the invention are those of the L series, formed from L lactide, such as L 210 or 214 or L 210 S; the R series formed from racemic D,L-lactide, such as R 104, 202, 203, or 206-208; the G series formed from glycolide, such as G 205; copolymers of the LR series formed from L-lactide, such as LR 706 or 708; or DL-lactide with glycolide, such as RG 502H or 503H.

Where other modes of administration, such as topical administration, are desired, a skilled person may readily select other polymers suitable for the formation of nanoparticles without undue experimentation. An alternative polymer is a pharmaceutically acceptable copolymer formed from monomers selected from methacrylic acid, methacrylic acid esters, acrylic acid and acrylic acid esters. These polymers are commercially available from Rohm Pharma GmbH and are marketed under the trademark EUDRAGIT (Registered Trademark of Rohm Pharma GmbH, Darmstadt, Germany). An especially preferred polymer of the EUDRAGIT series in the 1:1- to 1:2-copolymer which is formed from monomers selected from methacrylic acid and methacrylic acid lower alkyl esters. Non-limiting examples include the 1:1- to 1:2-copolymer of methacrylic acid and methyl methacrylate. The 1:1-copolymers are marketed in the EUDRAGIT L series, such as L30-D55, 100 or L 30 D. The corresponding 1:2-copolymers are marketed in the EUGRAGIT S series, such as S 100. Another preferred polymer of EUDRAGIT series is the 1:1-copolymer of methacrylic acid and acrylic acid ethyl ester. This polymer is marketed under the product name EUDRAGIT L 100-55.

Another polymer which is suitable for the formation of nanoparticles in accord with the invention is polyvinyl acetate phthalate (PVAP) or a pharmaceutically acceptable cellulose derivative selected from hydroxypropyl methyl cellulose acetate succinate (HPMCAS), hydroxypropyl methyl cellulose phthalate (HPMCP), poly (ε-caprolactone), cellulose acetate phthalte (CAP) and cellulose acetate trimellitate (CAT) (composition: trimellityl 29%, acetyl 22%, moisture 1%, free acid (as phthalic acid) 0.5%). HPMCP is marketed by Carbomer, Inc. Commercially available HPMCP 50 (USP/NF type 220824) and HPMCP 55 (USP/NF type 200731) are especially preferred for the practice of the invention. CAP has been marketed under the trademark AQUATERIC (Registered Trademark of FMC Corp). CAT is commercially available from Fisher Scientific.

Table 1 provides a list of polymers that were found to be particularly suitable for the production of photosensitizer-loaded nanoparticles.

TABLE 1

Polyester polymers used for preparation of photosensitizer-loaded nanoparticles

| Polymer | PLA/PGLA Ratio | Molecular Weight |
|---------|----------------|------------------|
| RG502   | 50/50          | 12,000           |
| RG502H  | 50/50          | 12,000           |
| RG504H  | 50/50          | 48,000           |

TABLE 1-continued

Polyester polymers used for preparation of photosensitizer-loaded nanoparticles

| Polymer | PLA/PGLA Ratio | Molecular Weight |
|---|---|---|
| RG752 | 75/25 | 12,000 |
| RG755 | 75/25 | 63,000 |
| RG756 | 75/25 | 98,000 |
| R104 | 100 | 2,000 |
| R202 | 100 | 16,000 |
| R202H | 100 | 16,000 |
| R203 | 100 | 28,000 |

Photosensitizers for Incorporation into Nanoparticles

The methods of the invention may be practiced with a variety of hydrophobic photosensitizers, many of which are described in Redmond and Curtis (1999) Photochemistry and Photobiology 70(4): 391-475. Preferably the photosensitizer is capable of rapid localization in target tissue. Preferred photosensitizers have the general structure of a polypyrrolic macrocycle, and preferably are tetrapyrrolic macrocycles. Photosensitizers useful for the invention include, but are not limited to the general photosensitizer types of porphyrins, chlorins, bacteriochlorins, isobacteriochlorins, purpurins, texaphrins, hematoporphyrins, phthalocyanines and pheophorbides.

Additional examples of photosensitizers useful in the invention include, but are not limited to, green porphyrins disclosed in U.S. Pat. Nos. 5,283,255, 4,920,143, 4,883,790, 5,095,030, and 5,171,749; and green porphyrin derivatives, discussed in U.S. Pat. Nos. 5,880,145 and 5,990,149. Several structures of typical green porphyrins are shown in the above-cited patents, which also provide details for the production of the compounds. Other non-limiting examples of photosensitizers which may be useful in the invention are photosensitizing Diels-Alder porphryin derivatives, described in U.S. Pat. No. 5,308,608; porphyrin-like compounds, described in U.S. Pat. Nos. 5,405,957, 5,512675, and 5,726,304; bacteriochlorophyll-A derivatives, described in U.S. Pat. Nos. 5,171,741 and 5,173,504; chlorins, isobacteriochlorins and bacteriochlorins, as described in U.S. Pat. No. 5,831,088; meso-monoiodo-substituted tetramacrocyclic and meso substituted tripyrrane, described in U.S. Pat. No. 5,831,088; polypyrrolic macrocycles from meso-substituted tripyrrane compounds, described in U.S. Pat. Nos. 5,703,230, 5,883,246, 6,022,981, 5,919,923, and 5,883,246; and ethylene glycol esters, described in U.S. Pat. No. 5,929,105. Dimeric forms of the green porphyrin and dimeric or multimeric forms of green porphyrin/porphyrin combinations can also be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins. Of course combinations of two or more photosensitizers may be used in the practice of the invention. It is preferred that the absorption spectrum of the photosensitizer be in the visible range, typically between 350 nm and 1200 nm, more preferably between 400-900 nm, and even more preferably between 600-900 nm.

Preferred photosensitizers are the green porphyrins, more preferred are the benzoporphyrin derivative mono-acid (BPD-MA), EA6 and B3 (U.S. Pat. Nos. 5,929,105 and 5,990,149, respectively). BPD-MA, for example, is lipophilic and a potent photosensitizer. BPD-MA is a preferred candidate for use in the instant invention, but other BPDs such as EA6 (also known as QLT 0074) and B3, QLT 0069 or other derivatives may also be used.

Preferred green porphyrins have the basic structure:

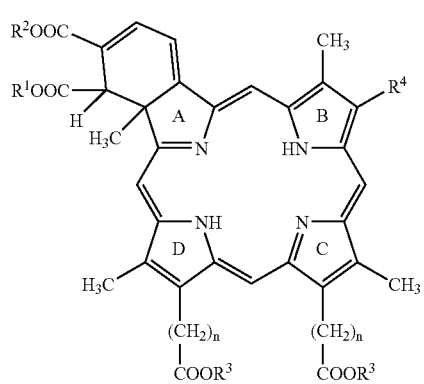

1 or

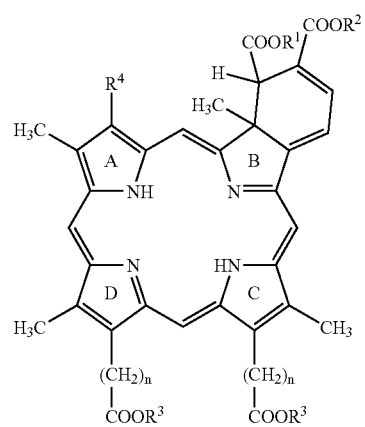

2 or

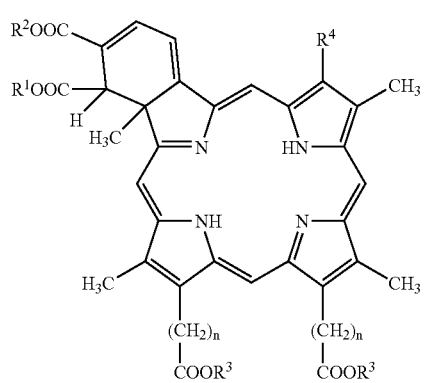

3 or

-continued

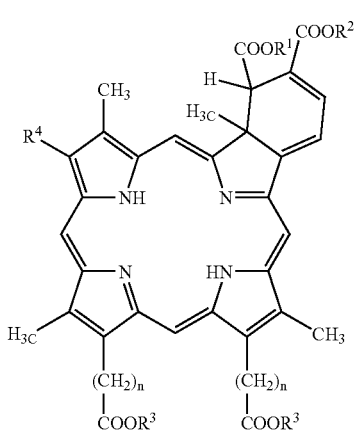

where $R^4$ is vinyl or 1-hydroxyethyl and $R^1$, $R^2$, and $R^3$ are H or alkyl or substituted alkyl, and n is an integer between 0 and 6, preferably 2.

BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MA$_C$ and BPD-MA$_D$, which are the components of verteporfin, as well as illustrations of A and B ring forms of EA6 and B3, are as follows:

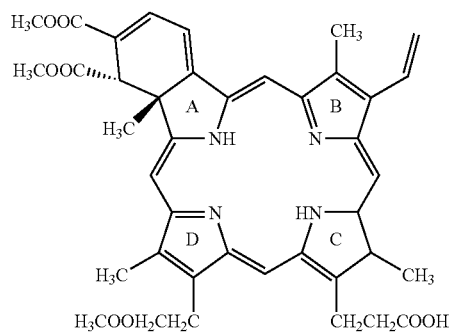

BPD-MA$_C$

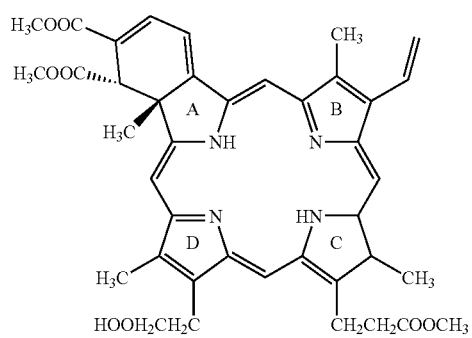

BPD-MA$_D$

-continued

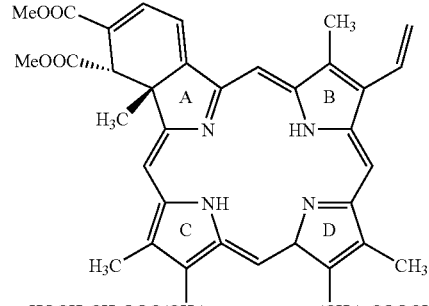

A-EA6

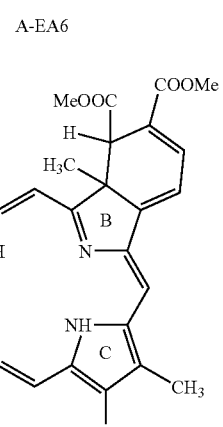

B-EA6

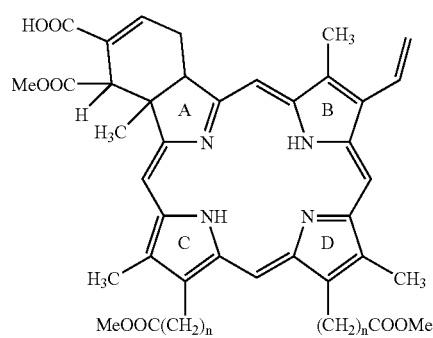

A-B3

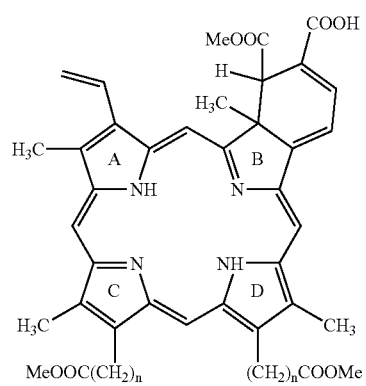

B-B3

Related compounds of formulas 3 and 4 are also useful; in general, $R^4$ will be vinyl or 1-hydroxyethyl and $R^1$, $R^2$, and $R^3$ are H or alkyl or substituted alkyl.

Additional examples of hydrophobic BPD B-ring compounds that are difficult to formulate, and are especially well suited to use in the invention are shown below, where the asterisks indicate chiral carbon positions.

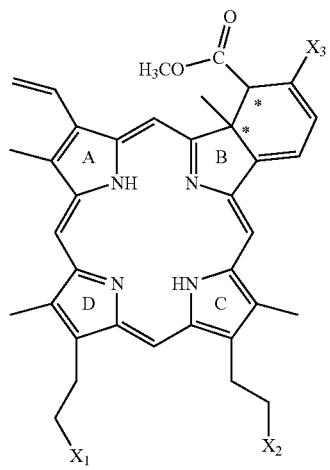

| Drug | X1 | X2 | X3 |
|---|---|---|---|
| QLT0060 | $CO(O(CH_2)_2)OH$ | $CO(OCH_2)_2)OH$ | $COOCH_3$ |
| QLT0069 | $COOCH_3$ | $COOCH_3$ | $COOH$ |
| QLT0078 | $CO(O(CH_2)_2)_2OH$ | $CO(O(CH_2)_2)_2OH$ | $COOCH_3$ |
| QLT0080 | $CO(O(CH_2)_2)_3OH$ | $CO(O(CH_2)_2)_3OH$ | $COOCH_3$ |
| QLT0081 | $CO(O(CH_2)_2)_2OCH_3$ | $CO(O(CH_2)_2)_2OCH_3$ | $CO(O(CH_2)_2)_2OCH_3$ |
| QLT0082 | $CO(O(CH_2)_2)_2OH$ | $CO(O(CH_2)_2)_2OH$ | $CO(O(CH_2)_2)_2OH$ |
| QLT0083 | $CO(O(CH_2)_2)_3OH$ | $CO(O(CH_2)_2)_3OH$ | $CO(O(CH_2)_2)_3OH$ |
| QLT0087 | $CO(O(CH_2)_2)_4OH$ | $CO(O(CH_2)_2)_4OH$ | $COOCH_3$ |
| QLT0088 | $COOCH_3$ | $COOCH_3$ | $CONH(C_6H_4)(C_5H_{10}N)$ |
| QLT0090 | $CO(O(CH_2)_2)_5OH$ | $CO(O(CH_2)_2)_5OH$ | $COOCH_3$ |
| QLT0093 | $CO(O(CH_2)_2)_5OH$ | $CO(O(CH_2)_2)_5OH$ | $CO(O(CH_2)_2)_5OH$ |

Additionally, the photosensitizers used in the invention may be conjugated to various ligands to facilitate targeting to the target tissue. These ligands include those that are receptor-specific as well as immunoglobulins and fragments thereof. Preferred ligands include antibodies in general and monoclonal antibodies, as well as immunologically reactive fragments of both.

The present invention is applied with particular advantage in situations where the photosensitizer is hydrophobic and thus not readily administered or used in PDT treatment of subjects. Of course, the photosensitizers of the invention may be formulated into nanoparticles for administration as a single photosensitizing agent as a mixture of more than one photosensitizing agent.

Preparation of Photosensitizer-Loaded Nanoparticles

Various methods of preparing drug-loaded nanoparticles are known (see Allémann et al. (1993) Eur. J. Pharm Biopharm 39(5), 173-191, which is incorporated by reference in its entirety). Especially preferred are the salting-out method and the emulsion method.

The salting-out technique developed by Bindschaedler, described in Bindschaedler et al (1998) J. Pharm. Sci. 77 (8): 696-698, was previously adapted for the preparation of drug-loaded nanospheres (see Alléman, Doctoral Thesis, University of Geneva, 1993). The technique involves the separation of a water-miscible solvent from an aqueous solution via a salting-out.

The nanoparticles of the invention may be prepared by first dissolving both photosensitizer drug and polymer in tetrahydrofuran (THF) or another organic solvent in which the components are soluble to form an organic phase. Depending on the solubility of the drug, other solvents that might be used include, but are not limited to acetic acid, dichloromethane, chloroform, N-methylpyrrolidone, acetone, ether, isopropanol, ter-butanol, ethanol, methanol, benzyl alcohol, ethyl acetate and propylene carbonate. The amount of photosensitizer added can be varied between about 1 and 20% (w/w) of the total weight of the combined photosensitizer and polyester polymer. If more than about 20% by weight of photosensitizer is added, the percent of the photosensitizer incorporated into the nanoparticles decreases, and drug is wasted. Preferably, the amount of added photosensitizer is between about 5 and about 15% and more preferably about 10% of the weight of the polyester polymer. More preferred is an amount of photosensitizer between about 5 and about 10% of the weight of the polymer.

An aqueous solution (aqueous phase) containing a water-soluble salt such as magnesium chloride (as a preferred embodiment) or magnesium acetate, and a hydrophilic polymer such as polyvinyl alcohol (PVAL) is then added to the above described organic phase. The PVAL acts as a stabilizing colloid. The mixture is then emulsified under vigorous mechanical agitation, for example, by magnetic stirring. Other forms of mechanical stirrer that might be used are a propeller stirrer, or stirrer fitted with a paddle, or stirrer fitter with a four branch helix, or other agitation means known in the art. Preferred are PVALs having a degree of hydrolysis of greater than 70%, and preferably greater than 85%. Suitable PVALs are marketed under the trademark MOWIOL® (Hoechst AG, Germany). Other hydrophilic polymers that could be used as an alternative to PVALs are Poloxamers, such as Poloxamer 407 (Pluronic F127) or Poloxamer 188 (Pluronic F68). The concentration of PVAL in the aqueous phase is in the range of about 5-20%, and more preferably about 10-15%. The water-soluble salt is included to facilitate the separation of the aqueous phase from the organic phase.

The invention includes the discovery that generally, a higher energy mechanical agitation favors the production of smaller nanoparticles. For example, at a stirring rate of 400 RPM, the nanoparticles formed tend to be larger, in the range of several thousand nm in diameter. Increasing the stirring rate to 800 RPM or above, and preferably to about 1800 RPM or above, tends to decrease the size of the nanoparticles formed. The amount of mechanical agitation to use with any particular device can be determined empirically by measuring the size of nanoparticles produced at intensity of agitation after a given time period, and then increasing the intensity or duration of agitation until the desired particle size is achieved.

The emulsion is diluted with a sufficient volume of water to enhance the diffusion of THF into the aqueous phase, inducing the formation of nanoparticles. The nanoparticles are purified by removal of residual THF and magnesium chloride by cross-flow filtration or other means known in the art.

In a typical protocol, a photosensitizer, e.g. BPD-MA or QLT 0069 was dissolved in 4.15 g THF. PLA (0.85 gm minus the weight of the photosensitizer used) was then dissolved in the THF under magnetic stirring to produce 5 gm of a viscous solution. Twenty grams of an aqueous phase containing 3 gm of PVAL and 12 g of $MgCl_2.6H_2O$ was added under vigorous magnetic stirring (2000 rpm) at room temperature (see Table 2). After the phase inversion, an oil-in-water emulsion was formed. The emulsion was stirred for 15 minutes to allow good homogenization. Subsequently, 40 gm of distilled water were added to induce the complete diffusion of THF into the aqueous phase, thus leading to the formation of nanoparticles.

TABLE 2

Typical formula of photosensitizer-loaded nanoparticles prepared by the salting out method

| | Percent by weight |
|---|---|
| Aqueous phase: | |
| $MgCl_2•6H_2O$ | 60% |
| PVAL (polyvinyl alcohol) | 15% |
| Distilled water | 25% |
| Organic phase: | |
| Polyester polymer e.g. PLA or PGLA | (17-X)% |
| Photosensitizer e.g. BPD-MA, QLT 0069 | X%, where X is between 1/100 and 1/3 of the weight of the polyester polymer |
| THF | 83% |

Nanoparticles can also be produced by an emulsification diffusion technique, as an alternative to the salting out process. An organic phase, such as PLGA and photosensitizer dissolved in benzyl alcohol (or another organic solvent in which the drug is soluble) is emulsified with an aqueous phase, preferably buffered, containing hydrophilic polymers such as PVAL by mechanical stirring at 2000 RPM for 15 minutes. Then water or buffer is added to the resulting emulsion under stirring in order to allow the complete diffusion of the solvent into the water and induce the formation of nanoparticles. A typical formula for the preparation of nanoparticles by the emulsification diffusion method is shown in Table 3.

TABLE 3

Typical formula of photosensitizer-loaded nanoparticles prepared by emulsification diffusion method

| | Percent by weight |
|---|---|
| Aqueous phase: | |
| Distilled water, Tris maleate buffer, pH 8.5 | 83% |
| PVAL (polyvinyl alcohol) | 17% |
| Organic phase: | |
| Polyester polymer e.g. PLGA | 4.10% |
| Photosensitizer e.g. QLT 0069 | 0.32% |
| Benzyl alcohol | 95.58% |

The nanoparticles produced by both the salting out and emulsion diffusion methods may be sterilized by filtration though a 0.22 micron filter, if a sterile preparation is desired. The invention includes the process parameters to produce nanoparticles of a sufficiently small size to facilitate efficient sterilization by filtration. The parameters include use of a stirring rate from 2000 to 8000 rpm; increasing the percentage of PVAL to be above 10% w/w; and increasing the stirring time to be longer than 5 minutes. Thus an initial set of process parameters to use is a stirring rate of 2000 rpm, 15% PVAL, and a stir time of 15 minutes using a concentration of 17% polyester polymer. Additional process parameters to reduce nanoparticle size include decreasing the amount of polyester polymer to be below 25% (which is equivalent to decreasing the viscosity of the organic phase by increasing solvent); nature of the organic solvent; the ratio of aqueous to organic phases; the choice of polyester polymer, the molecular weight of polyester polymer; and the pH of the aqueous phase.

Post production, nanoparticles may be freeze dried to prolong their shelf life, and thus the shelf life of the loaded photosensitizer. It is preferred to include a lyoprotectant before freeze drying to aid in the redispersion of the nanoparticles after freeze drying. The lyoprotectant may also help in maintaining a small size after freeze drying. Preferably, an amount of lyoprotectant is added so that the lyoprotectant/nanoparticle mass ratio is between 0/1 and 2/1. Suitable lyoprotectants include, but are not limited to, trehalose, lactose, glucose and mannitol. Trehalose is a preferred lyoprotectant.

Freeze dried photosensitizer-loaded nanoparticles may be reconstituted with a volume of sterile water that renders a concentration of photosensitizer in the range of 1 to 2 mg/ml prior to administering to a subject or other use.

Properties of Photosensitizer-Loaded Nanoparticles

Photosensitizer-loaded nanoparticles preferably have a mean diameter of less than 220 nm, although they may be larger if sterile filtration is not desired. Preferably, a preparation of nanoparticles has a mean diameter of less than about 200 nm, more preferably between about 100 nm and about 200 nm. The size of nanoparticles can be measured by a number of means known in the art for sizing small particles, including the use of a Nicomp™ particle sizer as described in Example 4, or a Coulter® Nano-Sizer (Coulter Electronics, Harpenden, Hertfordshire, UK).

Generally speaking, the concentration of photosensitizer in the nanoparticles depends on the nature of the photosensitizer used. When a green porphyrin, such as verteporfin or QLT 0069, is used, the amount of photosensitizer incorporated into the nanoparticle is preferably between about 1% by weight and about 20% by weight, and more preferably between about 3 and about 13% by weight, and even more preferably between about 3 and about 10% by weight.

The photosensitizer-loaded nanoparticles of the invention have the unexpected property of releasing the drug from the nanoparticle rapidly upon contact with serum or diluted serum. Without being limited to any particular theory, it is believed that the photosensitizer is transferred to serum proteins. Preferably, the nanoparticles release at least 50% of the photosensitizer within about five minutes, and preferably within about one to three minutes following contact with serum-containing medium. Serum-containing medium can be a medium containing from 1 to 100% bovine serum albumin (BSA) or human or other animal serum, or can be the blood or other bodily fluid of a human or other animal. Contact with serum-containing medium occurs when the photosensitizer-loaded nanoparticles are administered to a human subject undergoing photodynamic therapy. Alternatively, contact can be via administration of nanoparticles to bodily fluid, such as blood, withdrawn from an animal and optionally returned to the animal as part of a PDT treatment protocol. The rate of release of photosensitizer from nanoparticles can be determined by an assay similar to the one described in Example 6.

Formulations

Photosensitizer-loaded nanoparticles are conveniently formulated as sterile, freeze-dried powders containing trehalose or another lyoprotectant. A typical powder preferably contains a lyoprotectant/nanoparticle ratio in the range of about 0.1 to about 5, preferably in the range of about 0.6 to 3.0, and more preferably in the range of about 0.8 to 2.0 on a weight/weight basis. A sterile freeze-dried power containing nanoparticles and optional lyoprotectant may be reconstituted in an aqueous medium for administration to a human or other animal. The aqueous medium is preferably a pharmaceutically acceptable sterile medium, for example 5% dextrose or normal saline. Alternatively, the medium may be water for injection where the amount of lyoprotectant or other additive is sufficient to render the reconstituted material suitable for pharmaceutical or therapeutic use.

The photosensitizer-loaded nanoparticles of the invention may be formulated into a variety of additional compositions. These compositions may also comprise further components, such as conventional delivery vehicles and excipients including isotonising agents, pH regulators, solvents, solubilizers, dyes, gelling agents and thickeners and buffers and combinations thereof. Appropriate formulations and dosages for the administration of photosensitizers are known in the art. Suitable excipients for use with photosensitizers include water, saline, dextrose, glycerol and the like.

The particular concentration or amount of a given photosensitizer is adjusted according to its photosensitizing potency. For example, BPD-DA can be used but at about a five-fold higher concentration than that of BPD-MA. Suitable isotonising agents are preferably nonionic isotonising agents such as glycerol, sorbitol, mannitol, aminoethanol or propylene glycol as well as ionic isotonising agents such as sodium chloride. The solutions of this invention will contain the isotonising agent, if present, in an amount sufficient to bring about the formation of an approximately isotonic solution. The expression "an approximately isotonic solution" will be taken to mean in this context a solution that has an osmolarity of about 300 milliosmol (mOsm), conveniently 300+10% mOsm. It should be borne in mind that all components of the solution contribute to the osmolarity. The nonionic isotonising agent, if present, is added in customary amounts, i.e., preferably in amounts of about 1 to about 3.5 percent by weight, preferably in amounts of about 1.5 to 3 percent by weight. Summaries of pharmaceutical compositions suitable for use with photosensitizers are known in the art and are found, for instance, in *Remington's Pharmaceutical Sciences*.

Administration of and Use of Photosensitizer-Loaded Nanoparticles in Photodynamic Therapy The photosensitizer-loaded nanoparticles of the invention may be administered systemically or locally and may be used alone or as components of mixtures. The route of administration may be topical, intravenous, oral, subcutaneous, local (e.g. in the eye) or by use of an implant. For example green porphyrins-loaded photosensitizers may be administered by means including, but not limited to, topical preparations, intravenous injection or infusion, oral intake, or local administration in the form of intradermal injection or an implant. Additional routes of administration are subcutaneous, intramuscular, or intraperitoneal injections in conventional or convenient forms. For topical administration, the photosensitizer-loaded nanoparticles may be in standard topical formulations and compositions including lotions, suspensions or pastes.

The dose of photosensitizers may be optimized by the skilled person depending on factors such as, but not limited to, the photosensitizer chosen, the nature of the therapeutic protocol, the individual subject, and the judgment of the skilled practitioner. Preferred amounts of photosensitizers are those which are clinically or therapeutically effective in the treatment method being used. Such amounts are referred herein as "effective amounts".

It should be noted that the various parameters used for effective PDT in the invention are interrelated. Therefore, the dose should also be adjusted with respect to other parameters, for example, fluence, irradiance, duration of the light used in PDT, and time interval between administration of the dose and the therapeutic irradiation. With photosensitizers, for example, the form of administration, such as when coupled to a target-specific ligand, such as an antibody or an immunologically active fragment thereof, is one factor considered by a skilled artisan.

Depending on the needs of the subject and the constraints of the treatment method being used, smaller or larger doses of photosensitizers may be needed. For compositions which are highly specific to the target skin tissues and cells, such as those with the photosensitizer conjugated to a highly specific monoclonal antibody preparation or specific receptor ligand, dosages in the range of 0.005-10 mg/kg of body weight are suggested. For compositions, which are less specific to the target, larger dosages, up to 1-10 mg/kg, may be desirable. The preferred range for use in mice is from 0.05 mg/kg to 10 mg/kg. The useful range in humans for the photosensitizer will generally be lower than mice, such as from 0.005 mg/kg to 2 mg/kg. The foregoing ranges are merely suggestive in that the number of variables with regard to an individual treatment regime is large and considerable deviation from these values may be expected. The skilled artisan is free to vary the foregoing concentrations so that the uptake and stimulation/restoration parameters are consistent with the therapeutic objectives disclosed above.

In addition to human subjects, the present invention may be applied to non-human animals, such as mammals, particularly those important to agricultural applications (such as, but not limited to, cattle, sheep, horses, and other "farm animals"), industrial applications (such as, but not limited to, animals used to generate bioactive molecules as part of the biotechnology and pharmaceutical industries), and for human companionship (such as, but not limited to, dogs and cats).

Each photosensitizer requires activation with an appropriate wavelength of radiation. As such, the methods of the invention may be conducted with any irradiation, preferably in the range of visible light, which activates the photosensitizer used. Preferably, the irradiation contains one or more wavelengths which is capable of penetrating the skin to activate the photosensitizer used. The wavelength(s) of radiation or light useful in the invention depends on the activation range of the photosensitizer used as part of the treatment method. Wavelengths of about 380-900 nanometers (nm) are preferred, depending upon the photosensitizer and upon the depth of tissue penetration desired. More preferred are wavelengths from about 400 to about 900 nm, most preferred from about 400 to about 700 nm. For example, BPD-MA, a green porphyrin derivative, can be activated by red and blue light as well as ambient light containing wavelengths from 400-900 nm. Light having a wavelength shorter than 400 nm is acceptable, but not preferred because of the potentially damaging effects of UVA light.

An appropriate light source, preferably a laser or laser diode, in the range of about 550 to about 900 nm, depending on the absorption spectrum of the photosensitizer, may be used for photosensitizer activation. An appropriate and preferred wavelength for such a laser includes 690±12.5 nm at half-maximum when green porphyrins BPDs are used. The light dose administered during the PDT treatment contemplated herein can vary, and can range between about 0.1 to about 200 J/cm$^2$. The light dose is chosen depending on potency of the photosensitizer, the dosage of the photosensitizer and the purpose of the photodynamic treatment. When PDT is being conducted to ablate tumor tissue, then higher doses of irradiation, in the range of 100-250 J/cm$^2$ and sometimes even higher is generally desirable. When PDT is conducted to modulate an immune response, rather than killing target tissue, it is preferred that the irradiation be at low dose to reduce unwanted side effects while still activating the photosensitizer. The irradiation dose used (referred to as "low dose PDT") is preferably of lower intensity than that used for oncogenic treatment. A preferred range is from 0.1 to 20 J/cm$^2$.

When PDT is conducted to treat (choroidal) neovasculature in the eye (such as that associated with AMD), intermediate light doses, in the range of 20 to 100 J/cm$^2$ is generally used. For example, the dosage of light recommended for Visudyne® used in the treatment of AMD is 50 J/cm$^2$. Increases in irradiance may decrease the exposure times. Generally, a higher dose of photosensitizer will decrease the light dose required to exert a therapeutic effect.

The time of light irradiation after administration of the photosensitizer may be important as one way of maximizing the selectivity of the treatment, thus minimizing damage to structures other than the target tumor cells. Light treatment within three hours, and more preferably within an hour after administration of the photosensitizer should generally be used.

Unless defined otherwise all technical and scientific terms used herein have the same meaning as commonly understood to one of ordinary skill in the art to which this invention belongs.

Having now generally described the invention, the same will be more readily understood through reference to the following examples which are provided by way of illustration, and are not intended to be limiting of the present invention, unless specified.

EXAMPLE 1

Preparation of polymeric benzoporphyrin-Loaded Nanoparticles

Materials: The nanoparticles shown in the examples below were produced using three types of polyesters all with various molecular weight obtained from Boehringer Ingelheim (Ingelheim, Germany):
i) 50:50 PLGA (RG502 and RG502H (molecular weights (Mw)=12 000) and RG504H (Mw=48 000));
ii) 75:25 PLGA (RG752 (Mw=12 000), RG755 (Mw=63 000), and RG756 (Mw=98 000)) and
iii) pure PLA (R 104 (Mw=2 000), R202 and R202H (Mw 16 000) and R203 (Mw 28 000)).

Additional polyesters, shown in Table 1 may also be used.
Poly(vinyl alcohol) (PVAL) 87.7% hydrolysed with a Mw of 26 000 (Mowiol® 4-88) and 82.6% hydrolysed with a Mw of 18 000 (Mowiol® 3-83) (Hoechst, Frankfurt/Main, Germany) were selected as stabilizing colloid. Magnesium chloride hexahydrate (MgCl$_{2+}$6H$_2$O) (Fluka Biochemika, Buchs, Switzerland) was used as salting-out agent. Tetrahydrofuran (THF) (Merck, Darmstadt, Germany) and acetone (Fluka Biochemika, Buchs, Switzerland) were used as the organic water-miscible solvents. These solvents were chosen on the basis of previous work (Ibrahim et al., 1992; Allémann et al., 1992) and pharmaceutical properties with regard to toxicity (Witschi et al. 1997). D(+)-trehalose dihydrate (Sigma, St. Louis, Mo., USA), lactose monohydrate (Hänseler AG, Herisau, Switzerland), D(-)-mannitol (Riedel-de Haën®, Seelze, Germany) and D(+)-glucose anhydrous (Fluka Biochemika, Buchs, Switzerland) were used as lyoprotectants. All other chemicals were of analytical grade and used as such without further purification.

Methods: The possibility of producing very small nanoparticles was investigated using the salting-out process. The parameters were first chosen according to previous work (Ibrahim et al., 1992; Allémann et al., 1992; Allémann et al., 1993a) and were then varied in order to investigate the influence on particle mean size. Typically, 5 g of organic solution containing variable amounts of PLGA or PLA and a photosensitizer was added under mechanical stirring to 20 g of an aqueous phase containing PVAL, 60% (w/w) of a salting-out agent (MgCl$_{2+}$6H$_2$O). After the formation of an oil-in-water emulsion at room temperature, 60 ml of pure water was added to induce complete diffusion of the solvent into the aqueous phase, thus leading the formation of nanoparticles. Since the effectiveness of the sterile filtration process is also influenced by the microbial burden of the nanoparticle suspension to be filtered, water filtered through 0.1 µm membrane filter (Millipore®, MilliQ Academic, Switzerland) was routinely used for the preparation and the purification of the nanoparticles.

To obtain the conditions for the preparation of sub-200 nm nanoparticles, preliminary investigations were first performed using a THF solution containing 17% (w/w) of RG755 as organic phase. The particle size was evaluated as function of: a) the stirring rate (2000-13 500 rpm); b) stirring time of the emulsification (5-50 min); c) PVAL molecular weight (18 000-26000 Da); and PVAL percentage (10-15% (w/w)). The polymer percentage (10-17% (w/w)) was also varied.

Purification of the nanoparticle dispersions was by cross-flow filtration. Raw nanoparticles dispersions were purified by cross-flow filtration using a Sartocon® mini device fitted with ultrafiltration membrane with a molecular weight cut-off of 300 000 Da (Sartorius, Goettingen, Germany) to remove the soluble additives (THF, MgCl$_2$ and PVAL). Filtration was performed by adding volumes of water which were collected as filtrate fractions. The amount of eliminated PVAL in each filtrate fraction was determined by a calorimetric method.

EXAMPLE 2

Identification of Conditions that Favor Small Nanoparticle Production

Initial attempts to incorporate photosensitizers into polyester nanoparticles yielded nanoparticles that were too large for sterile filtration, in the range of 300 to 500 nm, or even higher if stirring rates in the range of 400-800 rpm were used to homogenize the organic and aqueous phases during nanoparticle formation. Various experiments were conducted in an attempt to identify conditions that produce nanoparticles having a mean diameter of less than 200 nm. The following parameters for the preparation of nanoparticles using the salting-out process was varied as indicated below, to achieve sub-200 nm nanoparticles.

| Aqueous phase | |
|---|---|
| Poly(vinyl alcohol) (PVAL) | 10% (w/w) |
| MgCl$_2$•6H$_2$O | 60% (w/w) |
| Distilled water | 30% (w/w) |

| Organic phase | |
|---|---|
| Polyester polymers | 17% (w/w) |
| Tetrahydrofuran (THF) | 83% (w/w) |
| Photosensitizer | variable |

The following parameters were used for the emulsion procedure.

| | |
|---|---|
| Aqueous/organic phase ratio | 1.5/1 |
| Stirring rate | 1800 rpm |
| Time of emulsification | 15 min |

The process parameters that decreased the mean particle size from 300 nm to sub-200 nm nanoparticles are:

Stirring rate: An increase in the stirring rate from 2,000 to 8,000 rpm led to a decrease of the size of R202 nanoparticles from 270 nm to 150.

Percentage of PVAL: At a stirring rate of 2,000 rpm, when the percentage of the PVAL was increased stepwise from 10 to 15% (w/w), the mean size of the nanoparticles was reduced from 275 to 148 nm.

Stirring time: increasing the stirring time during the emulsification from 5 to 15 min resulted in reduction of RG755 nanoparticle size from 198 to 148 nm.

With the following parameters of stirring rate 2,000 rpm, duration of emulsification 15 min, concentration of PVAL 15% and concentration of the polymer 17% as a starting point, additional process parameters that influence the particle size were identified as:

Percentage of the polymer: Decreasing the percentage of the polymer in organic phase (or decreasing the viscosity of the organic phase) from 25% to 10% (w/w) led to a 50% decrease in particle mean size (from 300 to 150 nm).

Nature of the organic solvent: RG504H nanoparticles with a mean size of 210 nm were obtained when acetone was used as solvent, while a mean size of 154 nm could be achieved with THF.

Aqueous/organic phase ratio: An increase in the aqueous/organic phase ratio from 1.5/1 to 4/1 enabled the production of the sub-200 nm nanoparticles.

Polymer properties (composition, molecular weight): sub-200 nm RG504H nanoparticles with a mean size of 154 nm could be produced, while using the same process parameters, large particles were obtained with RG504 polymer. Regarding caprolactone polymers, the particle mean size increase from 143 to 290 nm with increasing the polymer molecular weight from 13,000 to 80,000 Da.

Aqueous phase nature (influence of the pH of the aqueous phase): The pH of the aqueous phase (e.g. using tris maleate buffer (pH 8.5) as external phase, the preparation of QLT 0069-loaded nanoparticles with a particle size of 120 nm was possible while with pure distilled water as external phase, the final size was at least 500 nm.

EXAMPLE 3

Preparation of sub-200 nm Verteporfin-Loaded Nanoparticles

Nanoparticles containing verteporfin were prepared according to the protocol below, and their size and drug content analyzed.

| Component | % of phase by weight | grams |
|---|---|---|
| Aqueous phase | | |
| MgCl$_2$•6H$_2$0 | 60 | 12.0 |
| PVAL (Mowiol ® 3-83) | 15 | 3.0 |
| H$_2$0 distilled | 25 | 5.0 |
| Total weight of aqueous phase | | 20 |
| Organic phase | | |
| PLA | 15.3 | 0.8303 |
| Verteporfin | 1.7 | 0.0919 |
| THF | 83.0 | 3.6810 |
| Emulsification procedure | | |
| Aqueous phase | 20.0 g | |
| Organic phase | 5.43 g | |
| Stirring rate | 2,000 RPM | |
| Stirring time | 15 minutes | |
| Time of complete process | 20 minutes | |
| Freeze drying | | |
| 4 day cycle | | |
| Trehalose/nanoparticle ratio: 0.84 (w/w) | | |
| Nanoparticle characteristics | | |
| Mean size after freeze drying 139 +/− 3 nm | | |
| Drug loading: 7.0 +/− 0.7% | | |
| Entrapment efficiency: 70.2 +/− 6.7% | | |

EXAMPLE 4

Particle Size, Drug Retention and Sterilization of Verteporfin-Loaded Nanoparticles Drug retention was determined by passing the formulations through 0.22 micron Millex GV filters and the concentration of benzoporphyrin measured by spectrophotometry before and after filtration. Formulations were then stored for selected period at 2-8° C. and concentration of benzoporphyrin analyzed before and after 0.22 micron filtration.

The particle size was measured using photon correlation spectroscopy using a Coulter® Nano-Sizer™ (Coulter Electronics Harpenden, Hertforsdshire, UK), or Nicomp 380 particle sizer. Polydispersity index (PI) is an indication of the size distribution with values ranging from 0 to 9. The measurements were carried out at room temperature. The accuracy of the photon correlation spectrometer was confirmed by using polystyrene uniform latex standard particles (204±6 nm) (Duke Scientific Corp., Palo Alto, Calif., USA). Each value is the average of three measurements. The results are shown in Table 4.

a pore size of 0.45 μm before the sterilizing filtration process. Then, the pre-filtered sample was filtered through the appropriate sterilizing filter unit. Afterwards, 40 ml of sterile suspension was poured into 100 ml pre-weighed sterile glass vials under a laminar air-flow hood. In order to preserve the particles from contamination during the freeze-drying process, the vials were covered with sterile 0.22 μm membrane filters (Durapore hydrophobe, type GVHP, Millipore®, Volketswil, Switzerland). The sterile suspensions were frozen and freeze-dried as described below.

To determine if significant quantities of nanoparticles had been retained by the membrane, aliquots of the nanoparticle

TABLE 4

Influence of the nature of the solvent on the raw particle mean size and the viscosity of the organic phase (Aqueous phase: PVAL 15% (w/w), organic phase PLGA or PLA 17% (w/w), stirring rate 2000 rpm, stirring time of emulsification 15 min).

| Polymer | PLA/PGLA ratio | Mw | THF | | | Acetone | | |
|---|---|---|---|---|---|---|---|---|
| | | | viscosity (mPa·s)[a] | Mean size (nm)[b] | PI[c] | viscosity (mPa·s)[a] | Mean size (nm)[b] | PI[c] |
| RG502H | 50/50 | 12 000 | 3.6 ± 0.3 | 102 ± 4 | 2 | 2.5 ± 0.4 | 137 ± 13 | 3 |
| RG502 | 50/50 | 12 000 | 9.7 ± 0.1 | 125 ± 9 | 4 | 2.7 ± 0.3 | 173 ± 15 | 2 |
| RG504H | 50/50 | 48 000 | 47.7 ± 3.4 | 154 ± 17 | 4 | 17.6 ± 0.5 | 210 ± 66 | 2 |
| RG752 | 75/25 | 12 000 | 5.5 ± 0.3 | 132 ± 3 | 4 | 3.2 ± 0.5 | 120 ± 7 | 3 |
| RG755 | 75/25 | 63 000 | 49.9 ± 3.1 | 148 ± 5 | 2 | 20.2 ± 1.1 | 121 ± 10 | 4 |
| RG756 | 75/25 | 98 000 | 157.1 ± 6.3 | 152 ± 25 | 4 | 44.2 ± 2.5 | 145 ± 5 | 3 |
| R104 | 100/0 | 2 000 | 2.4 ± 0.3 | 152 ± 9 | 3 | 2.2 ± 0.3 | 143 ± 5 | 3 |
| R202 | 100/0 | 16 000 | 2.7 ± 0.3 | 138 ± 8 | 4 | 2.4 ± 0.2 | 183 ± 7 | 3 |
| R202H | 100/0 | 16 000 | 4.4 ± 0.3 | 166 ± 5 | 3 | 2.3 ± 0.3 | 174 ± 14 | 3 |
| R203 | 100/0 | 28 000 | 7.3 ± 0.2 | 145 ± 4 | 4 | 3.9 ± 0.3 | 184 ± 5 | 2 |

[a]Mean ± SD (n = 22)
[b]Mean ± SD (n = 3)
[c]PI: polydispersibility index, 0-9

To assess the redispersibility, 2 mg of freeze-dried nanoparticles were resuspended in 1 ml of distilled water under manual shaking for 30 s and the particle size was measured. The results are shown in Table 5.

TABLE 5

Analysis of Reconstituted Verteporfin Nanoparticle Formulations Containing PLGA Polymers, indicating verteporfin content of nanoparticles (mg/ml)

| | Batch RG755A | Batch RG755B |
|---|---|---|
| UV-Vis (mg/mL) (Unfiltered/Filtered) | | |
| Day 0 | 1.92/1.83 mg/ml | 1.32/1.31 mg/ml |
| Stored o/n @ 2-8° C. | 1.84/1.91 mg/ml | 1.32/1.29 mg/ml |
| Particle Size Analysis Mean Diameter (nm) | | |
| Day 0 | 114 nm | 112 nm |
| Stored o/n @ 2-8° C. | 112 nm | 110 nm |

The sterile filtration feasibility study first was conducted with a qualitative evaluation of different membrane filter systems. Three systems, Millex®-FG50 (hydrophobic polytetrafluoroethylene membrane), Swinnex®47 (hydrophilic Durapore membrane (GVWP04700)), Steriflip® (Express polyethersulfone membrane) (Millipore®, Volketswil, Switzerland), were tested. To avoid the possible clogging of the filtration device, the nanoparticle suspension containing a lyoprotectant was first pre-filtered through a membrane with dispersions taken before and after filtration were freeze-dried. The particle size distribution before and after filtration was also examined.

The sterility testing was performed on the freeze-dried nanoparticles, following European Pharmacopoeia guidelines (addendum 1999). The membrane filtration followed by incubation of the membrane in culture media was chosen as testing method. Typically, 50 mg of dried nanoparticles dispersed in 100 ml of sterile water were passed through a 0.22 micron membrane filter (47 mm in diameter). Then, the membrane was aseptically removed from the holder. After rinsing with three portions of sterile peptone solution, each half of the membrane was immersed in tubes containing appropriate media. Thioglycollate resazurine broth (BioMérieux®, Marcy, France) was used as aerobic or anaerobic medium for the detection of bacteria (except Bacillus subtilis, which grows in tripcase soy broth) and tripcase soy broth was used as medium for the detection of yeasts and fungi. Non-sterile membranes were used as positive controls. The tubes were incubated for 14 days at 32.5±2.5° C. (thioglycollate resazurine medium) or at 22.5±2.5° C. (tripease medium). The turbidity of the media was then observed over a basic period of 14 days in comparison to positive controls. The experiment was done two times.

Sterility testing was performed using the same conditions as just described above. Several categories of microorganisms were chosen for this test: *Staphylococcus aureus* (ATCC 6538), *Bacillus subtilis* (ATCC 6633) and *Pseudomonas aeruginosa* (ATCC 9027) as aerobic bacteria, *Clostridium sporogenes* (ATCC 11437) as anaerobic bacteria and *Can-* dida albicans (ATCC 10231) and *Aspergillus Niger* (ATCC 16404) as yeasts and fungi, respectively. Diluted cultures of each bacteria and fungi were prepared from the strains to obtain a final concentration of microorganisms less than 100 cfu/ml. After filtration of the nanoparticle suspensions in the same conditions used for the sterility testing, the final rinse was inoculated with 1 ml of microorganism solution. The samples were incubated as described above for 7 days.

All batches of nanoparticles tested showed no detectable visible growth of microorganisms, contrarily to positive controls for which a substantial increase of turbidity was systematically observed (data not shown). These observations suggested that sterile final nanoparticulate formulations had been achieved.

EXAMPLE 5

Characterization of Sterile Freeze-Dried Verteporfin-Loaded Nanoparticles

Various batches of verteporfin-loaded nanoparticles were prepared with 10% of initial verteporfin content. The nanoparticle suspensions were freeze dried in the presence of trehalose after sterile filtration. To check the reproducibility of the procedure, the batches were prepared in duplicate under the same conditions. To evaluate the effect of different amounts of trehalose on the size of verteporfin-loaded nanoparticles, each batch was divided into two aliquots. Regardless of the trehalose/nanoparticle ratio, complete redispersion was obtained after freeze-drying, and the particle size remained below 200 nm. The drug loading ranged from 6.7 to 8.8% (w/w) with different polymers, with entrapment efficiency reaching 91% with PLA nanoparticles. The results are shown in Table 6.

TABLE 6

Characterization of verteporfin-loaded nanoparticles after freeze drying and reconstitution

| Batch # | PLA/PGLA ratio | Initial drug content (%) | Drug loading | Entrapment efficiency (%) | Trehalose/nanoparticle ratio (w/w) | Mean size after freeze drying |
|---|---|---|---|---|---|---|
| RG755B | 75/25 | placebo | NA | NA | 2.1 | 139 +/− 2 |
| RG755Ca | 75/25 | 10.0 | 6.7 +/− 0.8 | 67.14 +/− 7.6 | 1.11 | 132 +/− 2 |
| RG755Ca | 75/25 | 10.0 | 7.0 +/− 0.7 | 70.18 +/− 6.7 | 0.68 | 134 +/− 6 |
| RG755Cb | 75/25 | 10.00 | 7.0 +/− 80.67 | 70.18 +/− 6.7 | 0.84 | 139 +/− 3 |
| R202B | 100 | placebo | NA | NA | 1.06 | 140 +/− 2 |
| R202Ca | 100 | 10.0 | 8.8 +/− 0.4 | 91.0 +/− 4.2 | 0.86 | 157 +/− 3 |
| R202Cb | 100 | 10.0 | 8.8 +/− 0.4 | 91.0 +/− 4.2 | 1.82 | 125 +/− 1 |
| R202Ca | 100 | 10.0 | 8.6 +/− 0.2 | 86.0 +/− 1.9 | 0.91 | 123 +/− 2 |
| R202Cb | 100 | 10.0 | 8.6 +/− 0.2 | 86.0 +/− 1.9 | 1.51 | 127 +/− 3 |

The concentration of verteporfin was determined by dissolving a precisely weighed amount of nanoparticles in 5 ml THF. The solution was shaken for 1 h at room temperature, and the concentration of verteporfin was determined spectophotometrically at 691 nm. Verteporfin solutions of known concentration were used to generate a calibration curve. The drug loading is defined as:

Drug loading (%)=(amount of drug in nanoparticles/amount of nanoparticles) X 100.

The drug entrapment efficiency represents the proportion of the initial amount of drug, which has been incorporated into nanoparticles. It is defined as:

Entrapment efficiency (%)=percent drug loading/percent of initial drug content) X 100.

EXAMPLE 6

Release of benzoporphyrin from Polymeric Nanoparticles

This example demonstrates that nanoparticles loaded with verteporfin (BPD-MA) is released from the nanoparticles within seconds of contact with serum proteins. The assay is based on the quenching of verteporfin fluorescence caused by tight packing in the nanoparticle formulation. The addition of serum results in transfer of verteporfin from the nanoparticle formulation to plasma proteins, accompanied by an increase of fluorescence. The rate of the transfer is of biological significance because drug retained by the formulation is not readily available to target cells and tissues and is likely less photodynamically active within the formulation.

Further increase of verteporfin fluorescence in this assay system could be achieved by addition of Triton X-100, which resulted in further monomerization of verteporfin and its dissociation from binding sites. With the addition of Triton, the fluorescence of verteporfin in the experimental mixture is maximal and can be used as a point of reference for determination of the magnitude of verteporfin transfer from formulation to plasma protein.

A sample of 100 μM (verteporfin concentration) was prepared by diluting the stock verteporfin nanoparticle sample with 5% dextrose solution (5DW). Fluorescence was excited with 440 nm and collected at 694 nm. Samples were maintained at 37° C. The excitation and emission shutters were released and the time-trace started(T=0 s). After 60 s, 0.2 mL of fetal bovine serum (FBS) was injected with a Hamilton glass syringe through a septum in the lid cover of the spectrometer. After an additional 180 s, 0.02 mL of 10% v/v Triton X-100 (in 5DW) was injected into the cuvette. Final concentrations of FBS and Triton X-100 were approximately 5% v/v and 0.05% v/v, respectively. Fluorescence readings were collected for another 180 s.

Figure 2:
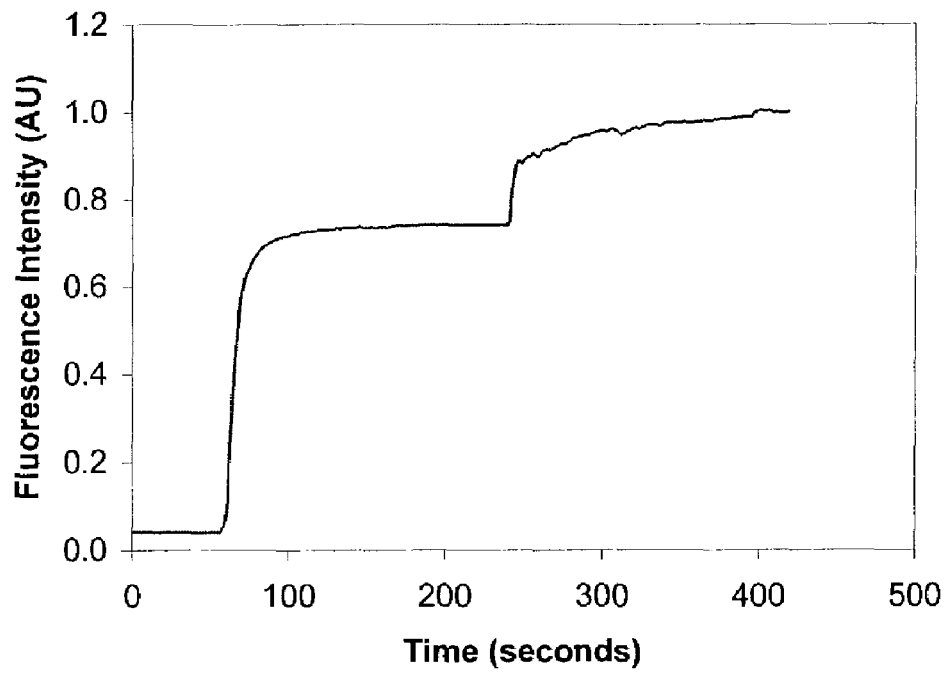
FIG. 2 is a graph showing overlayed time-traces showing the release of verteporfin from verteporfin-loaded nanoparticles. At t=60 s, 200 μL FBS was injected; at t=240 s, 20 μL 10% v/v Triton/5DW was injected.

During the first 60 s of each assay, the fluorescence of verteporfin within the nanoparticle formulation was reduced, due to self-quenching of photosensitizer formulation. Upon injection of FBS, the fluorescence rose and reached a plateau. The time required to reach a plateau, and the magnitude of the fluorescence observed at the plateau in comparison to the fluorescence of drug in Triton solution, gives an indication of the rate and efficiency of drug transfer to serum proteins. Verteporfin formulated in nanoparticles showed rapid transfer (FIG. 2). A mean value of this equilibrated fluorescence signal, labeled FFBS, was obtained by averaging fluorescence values from t=150 to 220 s. Following the injection of Triton X-100, the fluorescence signal rose further and eventually reached a plateau. A mean value of this new equilibrated fluorescence signal, labeled FTX, was obtained by averaging fluorescence values from t=300 to 420 s. The ratio FFBS/FTX gave an indication of the efficiency with which verteporfin was transferred to serum proteins from the lipid formulation. The mean value of FFBS/FTX (average of n=2 trials) was 0.76 (FIG. 2). These values would suggest that the majority of verteporfin were rapidly transferred to serum proteins within 150 sec.

EXAMPLE 7

Skin Fluorescence of benzoporphyrin from Polymeric Nanoparticles

Drug formulations were diluted with 5% dextrose to 174 μM (verteporfin) and intravenously injected into female SKH1 mice at 1.4 μmol/kg (active). Following injections, the mice were then kept in the dark or in subdued lighting.

Drug uptake was monitored by skin fluorescence using a Princeton Instruments non-invasive tissue fluorescence spectrophotometer equipped with a 5 mm diameter fluorescence probe connected to a liquid nitrogen cooled charge coupled device (LN/CCD) detector with spectrograph. Excitation was performed with an Oriel Fiber Optic Illuminator equipped with a 440 nm band pass filter for 5 sec. Fluorescence was collected from the mouse's skin over its right femoral leg muscle. Fluorescence signals were normalized to signals at 650 nm where drug fluorescence was expected to be minimal.

Figure 3:
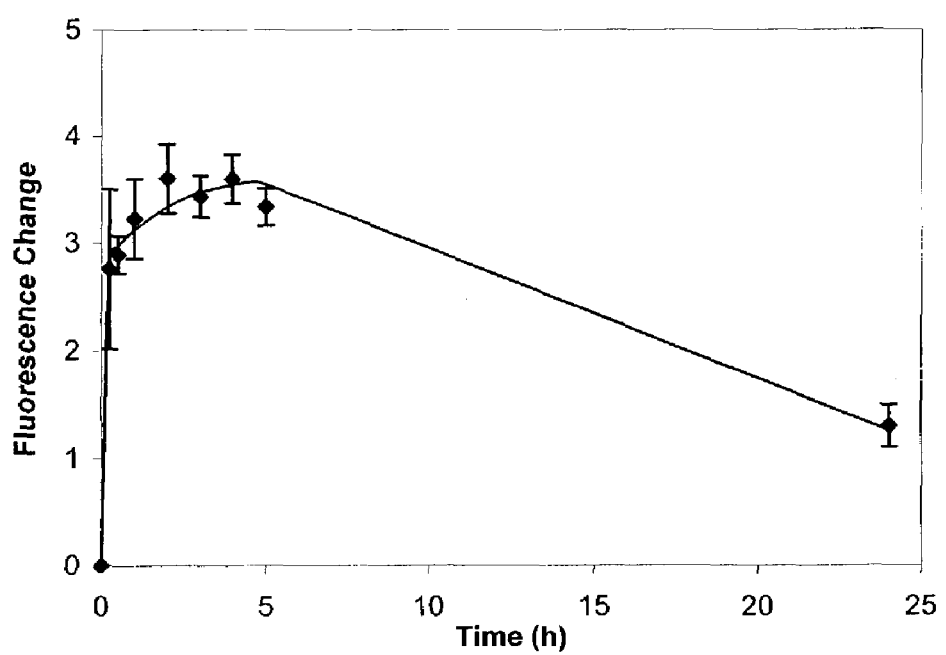
FIG. 3 is a graph showing the skin fluorescence in SKH1 female mice after administration of a 1.4 μmol/kg intravenous dose of verteporfin PLGA nanoparticles.

The results are shown in FIG. 3. The verteporfin fluorescence immediately increased after IV administration and then rapidly decreased over the next 24 hrs. Rapid clearance from the skin is desirable in a clinical setting.

EXAMPLE 8

Anti-Tumor Activity of verteporfin-Loaded Nanoparticles

Photosensitizer-loaded nanoparticle formulations were diluted with 5% dextrose to 174 μM (verteporfin) and injected intravenously into male M1-tumor-bearing DBA/2 mice at a dose of 1.4 μmol/kg. The tumor site was then exposed to 50 J/cm$^2$ of 690 nm light for 9 min and 20 s at 15, 30 or 60 min postinjection. The mice were monitored over 20 days for evidence of tumor control or cure.

A Spectra Physics Series 2000 Argon Ion Laser and a Coherent Dye Laser Model 599 were used in the study. The output wavelength of the laser was set at 690±3 nm (FWHM <1 nm). The microlens fiber optic lens was positioned to illuminate a 1 cm diameter area and the power output of the fiber optic was set at 70±6 mW (90 mW/cm$^2$ at target area). Exposure time was 9 min 20 s, which delivered a light dose of 50 J/cm$^2$. Anti-tumor activity of verteporfin formulated in a PLGA nanoparticle formulation (YK000814RG755A) was assessed in DBA/2 mice using an M1 tumor model. Table 7 shows the tumor bioassay results of male DBA/2 mice intravenously administered 1.4 μmol/kg active and exposed to 690 nm light at 50 J/cm2 for 9 min and 20 s. Early irradiation times at 15 and 30 min had improved tumor control compared to irradiation at 60 min.

TABLE 7

Results of Tumor Bioassay - Number of Tumor-free Animals

| Treatment | Time Delay | # of Mice Tumor-free | | | |
|---|---|---|---|---|---|
| | | Day 3 | Day 7 | Day 14 | Day 20 |
| verteporfin nanoparticles | 15 min | 3/3 | 3/3 | 2/3 | 2/3 |
| | 30 min | 3/4 | 3/4 | 3/4 | 3/4 |
| | 60 min | 3/3 | 3/3 | 1/3 | 1/3 |

EXAMPLE 9

Skin Photosensitivity After Administration of verteporfin-Loaded Nanoparticles

SKH1 female mice were injected intravenously (IV) with 1.4 μmol/kg of verteporfin-loaded nanoparticles (Batch YK000814RG755A). The animals were then immobilized with an intraperitoneal injection of Ketamine (50-100 mg/kg)/Valium (5 mg/kg) and immediately placed on a suspension bed, covered with aluminum foil and exposing a 1 cm circle over the right left flank.

At the 15 and 60 min post-injection timepoints, the 1 cm circular area on the flank was exposed to a solar simulator (light dose 60 J/cm$^2$) for 10 min per flank. The exposed surface was scored using parameters described in Table 8, on Day 1 and 3 following light exposure. Scores were based on erythema, eschar and edema formation. After Day 3 scoring, the mice were euthanized.

TABLE 8

Skin Photosensitivity Scoring Chart
Total Skin Photosensitivity Score is the Sum of Scores from Erythema, Eschar and Edema Observations

| | Description for Erythema and Eschar Formation |
|---|---|
| 0 | No observable reaction |
| 1 | Hardly detectable |
| 2 | Slight - visible pale pink, no vessels broken, no red spots |
| 3 | Blanching - few broken vessels, no eschar formation |
| 4 | Erythema - more broken vessels, leading to yellow eschar formation |
| 5 | Severe - many broken vessels, eschar formation - but less than 50% of site |
| 6 | Very severe - rosette, eschar formation on more than 50% of site |
| | Edema |
| 1 | Slight within exposure site |
| 2 | Mild within exposure site (skin fold less than 1 mm) |
| 3 | Moderate - (skin fold measurement 1-2 mm thickness) |
| 4 | Severe - extending beyond exposure side (skin fold measurement > 2 mm thickness) |

(minimum score = 0, maximum score = 10)

Figure 4:
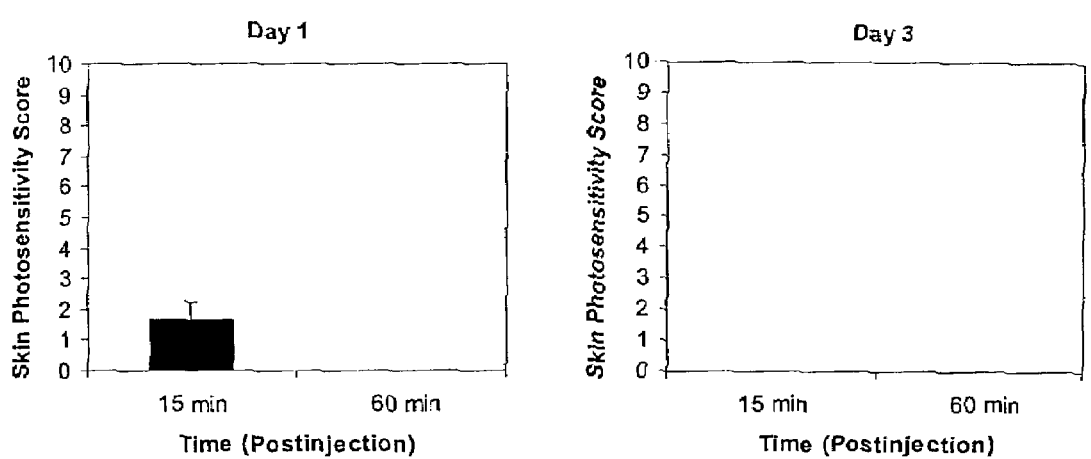
FIG. 4 are graphs showing skin photosensitivity induced by verteporfin-loaded nanoparticles administered intravenously, exposed to light from a solar simulator, and scored 1 and 3 days post injection. Intravenous dose of verteporfin was 1.4 μmol/kg; light dose was 60 $J/cm^2$. Error bars indicate standard deviation based on four mice per group.

Female SKH-1 mice displayed low levels of skin photosensitivity after being intravenously injected with 1.4 μmol/kg of verteporfin nanoparticles YK00814RG755A and exposed to solar simulator light for 10 min. Skin photosensitivity arising from exposure to the solar simulator was highest at the earliest timepoint tested (15 min) and decreased with time after injection (FIG. 4). Signs of any erythema, eschar and edema had diminished by Day 3 supporting the rapid clearance of verteporfin delivered in nanoparticles. Rapid clearance of photosensitizer is desirable in the clinical setting.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

References

Allémann, E., Doelker, E., Gurny, R., 1993a. Drug loaded poly(lactic acid) nanoparticles produced by a reversible salting-out process: purification of an injectable dosage form. Eur. J. Pharm. Biopharm., 39, 13-18.

Allémann, E., Gurny, R., Doelker, E., 1992. Preparation of aqueous polymeric nanodispersions by a reversible salting-out process: influence of process parameters on particle size. Int. J. Pharm., 87, 247-253.

Allémann, E., Leroux, J. C., Gurny, R., 1998. Biodegradable nanoparticles of poly(lactic acid) and poly(lactic-co-glycolic acid) for parenteral administration. In: Lieberman, H. A., Rieger, M. M., Banker, G. S. (Eds.), Pharmaceutical dosage forms: disperse systems. Marcel Dekker, Inc, New York, 3, 163-193.

Allémann, E., Leroux, J. C., Gurny, R., Doelker, E., 1993b. In vitro extended-release properties of drug-loaded poly(D,L-lactic acid) nanoparticles produced by a salting-out procedure. Pharm. Res., 10, 1732-1737.

Athanasiou, K. A., Niederauer, G. G., 1996. Sterilization, toxicity, biocompatibility and clinical applications of polylactic acid/polyglycolic acid copolymers. Biomaterials, 17, 93-102.

Auvillain, M., Cavé, G., Fessi, H., Devissaguet, J. P., 1989. Lyophilisation de vecteurs colloïdaux submicroniques. S. T. P. Pharma., 5, 738-744.

Bugada, D. C., Rudin, A., 1985. Characterization of poly (vinyl alchol). J. App. Polym. Sci., 30, 4137-4147.

Carpenter, J. F., Pikal, M. J., Chang, B. S., Randolph, T. W., 1997. Rational design of stable lyophilized protein formulations: some practical advice. Pharm. Res., 14, 969-974.

De Chasteigner, S., Cavé, G., Fessi, H., Devissaguet, J. P., Puisieux, F., 1996. Freeze-drying of itraconazole-loaded nanosphere suspensions: a feasibility study. Drug Dev. Res., 116-124.

De Chasteigner, S., Fessi, H., Cavé, G., Devissaguet, J. P., Puisieux, F., 1995. Gastro-intestinal tolerance study of a freeze-dried oral dosage form of indomethacin-loaded nanocapsules. S. T. P. Pharma Sciences, 5, 242-246.

DeLuca, P. P., Boylan, J. C., 1984. Formulation of small volume parenterals. In: Avis, K. E., Lachman, L., Lieber-mann, H. A. (Eds.), Pharmaceutical dosage forms: parenteral medications. M DEKKER, Inc., New York, 1, 139-201.

Douglas, S. J., Davis, S. S., Illum, L., 1987. Nanoparticles in drug delivery. CRC Crit. Rev. in Ther. Drug Carrier Syst., 3, 233-260.

Dunn, R. L., English, J. P., Strobel, J. D., Cowsar, D. R., Tice, T. R., 1988. Polymers in medicine III. Elsevier Science Publishers B. V., Amsterdam.

Finley, J. H., 1961. spectrophotometric determination of polyvinyl alcohol in paper coatings. Anal. chem., 33, 1925-1927.

Ford, A. W., Dawson, P. J., 1993. The effect of carbohydrate additives in the freeze-drying of alkaline phosphatase. J. Pharm. Pharmacol., 45, 86-93.

Goldbach, P., Brochart, H., Wehrlé, P., Stamm, A., 1995. Sterile filtration of liposomes: retention of encaspsulation carboxyfluorescein. Int. J. Pharm., 117, 225-230.

Hausberger, A. G., Kenley, R. A., DeLuca, P. P., 1995. Gamma irradiation effects on molecular weight and in vitro degradation of poly(D,L-lactide-co-glycolide) microspheres. Pharm. Res., 12, 851-856.

Ibrahim, H., Bindschaedler, C., Doelker, E., Buri, P., Gurny, R., 1992. Aqueous nanodispersions prepared by salting-out process. Int. J. Pharm., 87, 239-246.

Jefferey, H., Davis, S. S., O'Hagan, D. T., 1991. The preparation and characterisation of poly(lactide-co-glycolide) microparticles. I: oil-in water emulsion solvent evaporation. Int. J. Pharm., 77, 169-175.

Kawashima, Y., Yamamoto, H., Takeuchi, H., Hino, T., Niwa, T., 1998. Properties of a peptide containing DL-lactide/glycolide copolymer nanospheres prepared by novel emulsion solvent diffusion methods. Eur. J. Pharm. Biopharm., 45, 41-48.

Kreuter, J., 1983. Evaluation of nanoparticles as drug-delivery systems III: materials, stability, toxicity, possibilities of targeting, and use. Pharma. Acta Helv., 58, 242-249.

Krishnamurthy, R., Lumpkin, J. A., 1998. Stability of proteins during manufacture and release from biodegradable polymers. Pharm. Techn., 28-34.

Lee, S. C., Oh, J. T., Jang, M. H., Chung, S. I., 1999a. Quantitative analysis of polyvinyl alcohol on the surface of poly(D,L-lactide-co-glycolide) microparticles prepared by solvent evaporation method: effect of particle size and PVA concentration. J. Control. Res., 59, 123-132.

Leroux, J. C., Allémann, E., Doelker, E., Gurny, R., 1995. New approach for the preparation of nanoparticles by an emulsification-diffusion method. Eur. J. Pharm. Biopharm., 41, 14-18.

Lidgate, D. M., Trattner, T., Shultz, R. M., Maskiewicz, R., 1992. sterile filtration of a parenteral emulsion. Pharm. Res., 9, 860-863.

Mauduit, J., Vert, M., 1993. Les polymères à base d'acides lactique et glycolique et la délivrance contrôlée des principes actifs. S. T. P. Pharma. Sciences, 3, 197-212.

Mohr, D., Wolff, M., Kissel, T., 1999. Gamma irradiation for terminal sterilization of 17□-estradiol loaded poly-(D,L-lactide-co-gylcolide) microparticles. J. Control. Rel, 61, 203-217.

Montanari, L., Costantini, M., Signoretti, E. C., Valvo, L., Santucci, M., Bartolomei, M., Fattibene, P., Onori, S., Faucitano, A., Conti, B., Genta, I., 1998. Gamma irradiation effects on poly(D,L-lactide-co-gylcolide) microspheres. J. Control. Rel., 56, 219-229.

Quintanar-Guerrero, D. Etude de nouvelles techniques d'obtention de suspensions de nanoparticules à partir de polymères préformés. 1997. University of Geneva. Ref Type: Thesis/Dissertation Quintanar-Guerrero, D., Fessi, H., Allémann, E., Doelker, E., 1996. Influence of stabilizing agents and preparative variables on the formation of poly(D,L-lactic acid) nanoparticles by an emulsification-diffusion technique. Int. J. Pharm., 143, 133-141.

Randolph, T. W., 1997. Phase separation of excipients during lyophilization: Effects on protein stability. J. Pharm. Sci., 86, 1198-1202.

Reich, G., 1998. Ultrasound-induced degradation of PLA and PLGA during microsphere processing: influence of formulation variables. Eur. J. Pharm. Biopharm., 45, 171.

Rodrigues Jr, J. M., Fessi, H., Bories, C., Puisieux, F., Devissaguet, J. P., 1995. Primaquine-loaded poly(lactide) nanoparticles: physicochemical study and acute tolerance in mice. Int. J. Pharm., 126, 253-260.

Rothen-Weinhold, A., Besseghir, K., Gurny, R., 1997. Analysis of the influence of polymer characteristics and core loading on the in vivo release of a somatostatin analogue. Eur. J. Pharm. Sci., 5, 303-313.

Sah, H., Chien, Y. W., 1995. Role of low-molecular-weight polylactide and its copolymer in the acceleration of hydrolysis of PLGA(75:25) microcaspsules. Proceed. Intern. Symp. Control. Rel. Bioact., 22, 776-777.

Scholes, P. D., Coombes, A. G. A., Illum, L., Davis, S. S., Vert, M., Davies, M. C., 1993. The preparation of sub-200 nm poly(lactide-co-glycolide) microspheres for site-specific drug delivery. J. Control. Rel., 25, 145-153.

Smith, A., Hunneyball, I. M., 1986. Evaluation of poly (lactic acid) as a biodegradable drug delivery system for parenteral administration. Int. J. Pharm., 30, 215-220.

Snowman, J. W., 1991. Freeze drying of sterile products. In: Groves, M. J., Olson, W. P., Anisfeld, M. H. (Eds.), Sterile pharmaceutical manufacturing: applications for the 1990's. Interpharm Press, 1, 79-108.

Tracy, M. A., Firouzabadian, L., Zhang, Y., 1995. Effects of PLGA end groups on degradation. Proceed. Intern. Symp. Control. Rel. Bioact. Mater., 22, 786-787.

Tracy, M. A., Ward, K. L., Firouzabadian, L., Wang, Y., Dong, N., Qian, R., Zhang, Y., 1999. Factors affecting the degradation rate of poly(lactide-co-glycolide) microspheres in vivo and in vitro. Biomaterials., 20, 1057-1062.

Vert, M., 1987. Structure et comportement des polymères. Exemples des polymères biorésorbables. S. T. P. Pharma., 3, 216-222.

Vert, M., Schwach, G., Engel, R., Coudane, J., 1998. Something new in the field of PLA/GA bioresorbable polymers? J. Control. Rel., 53, 92.

Volland, C., Wolff, M., Kissel, T., 1994. The influence of terminal gamma-sterilization on captopril containing poly(D, L-lactide-co-glycolide) microspheres. J. Control. Rel., 31, 293-305.

Witschi, C., Doelker, E., 1997. Residual solvents in pharmaceutical products: acceptable limits, influences on physicochemical properties, analytical methods and documented values. Eur. J. Pharm. Biopharm., 43, 215-242.

Zheng, J. Y., Bosch, H. W., 1997. Sterile filtration of Nanocrystal™ drug formulations. Drug Dev. Ind. Pharm., 23, 1087-1093.

The invention claimed is:

1. A photosensitizer-loaded nanoparticle comprising one or more green porphyrins and one or more polymers of poly (D,L-lactide-co-glycolide), poly(D,L-lactide), or a combination thereof, wherein the porphyrin is rapidly released from the nanoparticle upon introduction into a serum-containing environment.

2. The nanoparticle of claim 1, wherein said one or more green porphyrins is selected from BPD-MA, QLT 0074 or QLT 0069.

3. The nanoparticle of claim 1 wherein the polymer is poly(D,L-lactide).

4. The nanoparticle of claim 1 wherein the polymer is poly(D,L-lactide-co-glycolide).

5. The nanoparticle of claim 1 having a mean diameter of less than 200 nm.

6. The nanoparticle of claim 1 having a mean diameter of between 100 and 200 nm.

7. The nanoparticle of claim 1 additionally comprising a lyoprotectant.

8. The nanoparticle of claim 7, wherein the lyoprotectant is trehalose.

9. The nanoparticle of claim 1 in a freeze dried form.

10. The nanoparticle of claim 1, wherein the green porphyrins comprise from about 1% to about 20% by weight of the nanoparticle.

11. The nanoparticle of claim 10 wherein the green porphyrins comprises from about 5 to about 10% by weight of the nanoparticle.

12. The nanoparticle of claim 1, wherein the nanoparticles release at least 50% of the porphyrin within one minute of contacting a serum-containing medium.

13. The nanoparticle of claim 12 wherein the serum-containing medium is a bodily fluid of an animal.

14. The nanoparticle of claim 13 wherein the serum-containing medium is human blood.

15. The nanoparticle of claim 13 having a mean particle size of less than 200 nm in diameter.

16. The nanoparticle of claim 13 wherein the mean particle size is between about 100 nm and 200 nm in diameter.

17. A composition comprising the nanoparticle of claim 1.

18. The nanoparticle of claim 1 having a mean diameter of about 200 nm.

19. The nanoparticle of claim 13 having a mean particle size of about 200 nm in diameter.

* * * * *